US011596485B2

(12) United States Patent
Ohashi et al.

(10) Patent No.: US 11,596,485 B2
(45) Date of Patent: Mar. 7, 2023

(54) METHOD OF REMOTELY SUPPORTING SURGERY ASSISTANT ROBOT AND REMOTE SUPPORT SYSTEM

(71) Applicants: SYSMEX CORPORATION, Kobe (JP); MEDICAROID CORPORATION, Kobe (JP)

(72) Inventors: Masanao Ohashi, Kobe (JP); Takehiko Sudoh, Kobe (JP); Shoko Ito, Kobe (JP); Jota Ida, Kobe (JP); Yasuyuki Fukuda, Kobe (JP)

(73) Assignees: SYSMEX CORPORATION, Kobe (JP); MEDICAROID CORPORATION, Kobe (JP)

( * ) Notice: Subject to any disclaimer, the term of this patent is extended or adjusted under 35 U.S.C. 154(b) by 0 days.

(21) Appl. No.: 16/592,819

(22) Filed: Oct. 4, 2019

(65) Prior Publication Data
US 2020/0107891 A1 Apr. 9, 2020

(30) Foreign Application Priority Data
Oct. 6, 2018 (JP) .............................. JP2018-190527

(51) Int. Cl.
*A61B 34/30* (2016.01)
*A61B 90/00* (2016.01)
(Continued)

(52) U.S. Cl.
CPC ............ *A61B 34/30* (2016.02); *A61B 90/361* (2016.02); *B25J 9/1697* (2013.01); *G06T 1/0014* (2013.01);
(Continued)

(58) Field of Classification Search
CPC ....... A61B 34/30; A61B 90/361; G16H 40/67
See application file for complete search history.

(56) References Cited

U.S. PATENT DOCUMENTS

| 5,038,089 A | * | 8/1991 | Szakaly | ............... | G05B 19/427 |
| | | | | | 318/573 |
| 5,305,427 A | * | 4/1994 | Nagata | .................. | B25J 19/023 |
| | | | | | 700/254 |

(Continued)

FOREIGN PATENT DOCUMENTS

| JP | 2003-22326 A | 1/2003 |
| JP | 2005-111080 A | 4/2005 |

(Continued)

OTHER PUBLICATIONS

The extended European search report (EESR) dated Mar. 12, 2020 in a counterpart European patent application.

(Continued)

*Primary Examiner* — Peter D Le
(74) *Attorney, Agent, or Firm* — Metrolex IP Law Group, PLLC

(57) ABSTRACT

A method for remotely supporting a surgery assistant robot may include: receiving at least one piece of operation information concerning an operation of the surgery assistant robot, by a server device that performs a remote support for the surgery assistant robot; and transmitting, in response to a predetermined event, at least one of a sound, an image, or a text from the server device to at least one of the surgery assistant robot or a terminal device.

23 Claims, 20 Drawing Sheets

(51) Int. Cl.
  *G16H 40/67* (2018.01)
  *G16H 30/40* (2018.01)
  *B25J 9/16* (2006.01)
  *G06T 1/00* (2006.01)
  *H04N 23/80* (2023.01)
  *H04N 23/50* (2023.01)

(52) U.S. Cl.
  CPC ............ *G16H 30/40* (2018.01); *G16H 40/67* (2018.01); *H04N 23/815* (2023.01); *G05B 2219/45117* (2013.01); *H04N 23/555* (2023.01)

(56) References Cited

U.S. PATENT DOCUMENTS

| | | | | | |
|---|---|---|---|---|---|
| 5,624,398 | A * | 4/1997 | Smith | | B25J 3/04 604/95.01 |
| 5,838,428 | A * | 11/1998 | Pipitone | | G01S 17/46 356/3.09 |
| 6,288,838 | B1 * | 9/2001 | Ito | | G02B 21/22 359/363 |
| 7,373,218 | B2 * | 5/2008 | Sakagami | | H04N 7/181 700/245 |
| 7,626,569 | B2 * | 12/2009 | Lanier | | G06F 1/1601 345/156 |
| 8,374,421 | B1 * | 2/2013 | Hickman | | B25J 9/1697 382/153 |
| 10,360,531 | B1 * | 7/2019 | Stallman | | G06Q 10/087 |
| 10,939,962 | B1 * | 3/2021 | Ellman | | A61B 90/361 |
| 2002/0018587 | A1 * | 2/2002 | Ueda | | G16H 30/40 382/128 |
| 2002/0082612 | A1 * | 6/2002 | Moll | | G09B 23/285 606/130 |
| 2003/0135203 | A1 * | 7/2003 | Wang | | A61B 34/37 606/1 |
| 2004/0114817 | A1 * | 6/2004 | Jayant | | H04N 19/126 382/239 |
| 2005/0041839 | A1 * | 2/2005 | Saitou | | H04N 1/00164 382/103 |
| 2006/0087746 | A1 * | 4/2006 | Lipow | | A61B 34/70 359/689 |
| 2006/0185091 | A1 * | 8/2006 | Jackson | | A61G 13/04 5/621 |
| 2006/0217841 | A1 * | 9/2006 | Matsumoto | | G05B 19/41815 700/248 |
| 2007/0005045 | A1 * | 1/2007 | Mintz | | A61B 34/74 606/1 |
| 2007/0167702 | A1 | 7/2007 | Hasser et al. | | |
| 2009/0163928 | A1 * | 6/2009 | Schena | | A61B 90/50 606/130 |
| 2009/0173846 | A1 * | 7/2009 | Katz | | A61B 90/50 248/124.1 |
| 2009/0268010 | A1 * | 10/2009 | Zhao | | A61B 1/00009 348/45 |
| 2010/0241693 | A1 * | 9/2010 | Ando | | G06Q 30/06 709/203 |
| 2011/0202968 | A1 * | 8/2011 | Nurmi | | G06F 21/10 726/1 |
| 2011/0306873 | A1 * | 12/2011 | Shenai | | A61B 8/0841 600/424 |
| 2012/0032882 | A1 * | 2/2012 | Schlachta | | G06F 3/0346 345/157 |
| 2012/0144336 | A1 * | 6/2012 | Pinter | | H04L 43/02 715/772 |
| 2012/0307027 | A1 * | 12/2012 | Popovic | | G06T 7/246 348/65 |
| 2012/0330613 | A1 * | 12/2012 | Sillman | | A61B 90/98 702/184 |
| 2013/0253940 | A1 * | 9/2013 | Zziwa | | G06Q 10/0635 705/2 |
| 2014/0051921 | A1 * | 2/2014 | Miller | | H04N 21/2402 600/103 |
| 2014/0150820 | A1 * | 6/2014 | Yoo | | A47L 11/4061 15/98 |
| 2014/0233815 | A1 * | 8/2014 | Sakaue | | G16H 30/20 382/128 |
| 2014/0240106 | A1 * | 8/2014 | Kodama | | G08B 1/08 340/286.07 |
| 2015/0256790 | A1 * | 9/2015 | Priest | | A61B 1/0005 348/441 |
| 2015/0278445 | A1 * | 10/2015 | Miura | | A61B 6/563 705/2 |
| 2015/0342689 | A1 * | 12/2015 | Kamon | | B25J 9/1689 606/130 |
| 2017/0165837 | A1 | 6/2017 | Asano et al. | | |
| 2019/0110856 | A1 * | 4/2019 | Barral | | G16H 30/40 |
| 2019/0200863 | A1 * | 7/2019 | Shelton, IV | | G06F 13/00 |

FOREIGN PATENT DOCUMENTS

| | | |
|---|---|---|
| JP | 2005-118232 A | 5/2005 |
| JP | 2017-104456 A | 6/2017 |
| WO | 2017/083768 A1 | 5/2017 |

OTHER PUBLICATIONS

Office Action dated Jul. 26, 2022 in a counterpart Japanese patent application, with English translation.

Nikkei Linux, "The Linux Kernel: Q&A48", Nov. 2015 issue, p. 34, vol. 17th, No. 11, Nikkei BP, Japan; Cited in the JPOA dated Jan. 24, 2023.

Office Action dated Jan. 24, 2023 in a counterpart Japanese patent application, with English translation.

* cited by examiner

FIG. 20
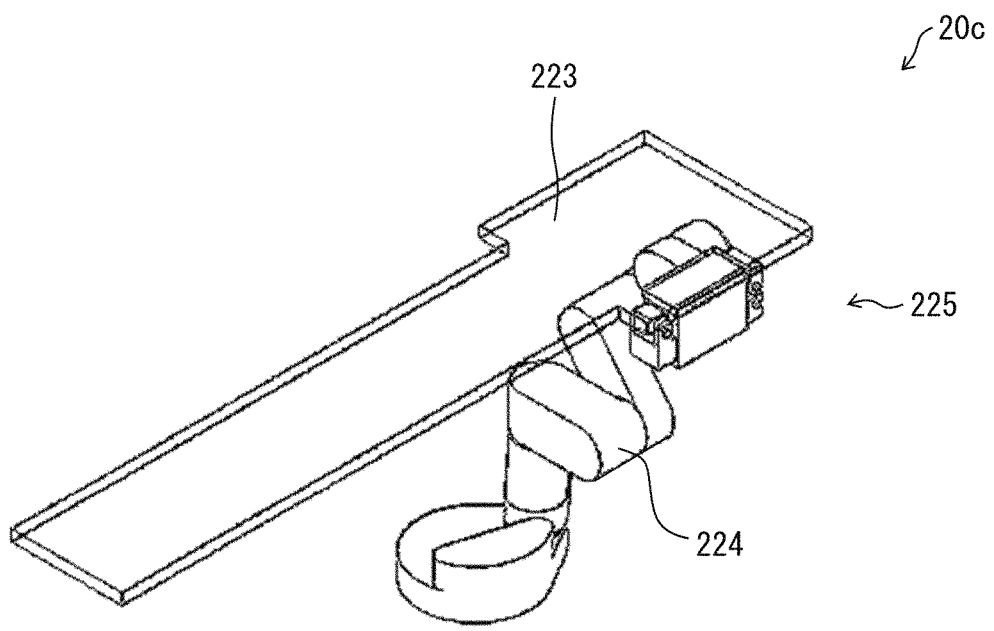
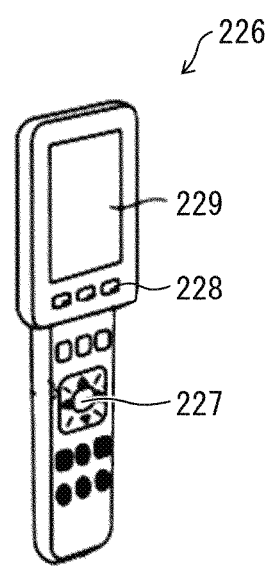

METHOD OF REMOTELY SUPPORTING SURGERY ASSISTANT ROBOT AND REMOTE SUPPORT SYSTEM

CROSS REFERENCE TO RELATED APPLICATIONS

This application claims priority from to prior Japanese Patent Application No. 2018-190527 filed with the Japan Patent Office on Oct. 6, 2018 the entire contents of which are incorporated herein by reference.

BACKGROUND

The disclosure relates to, for example, a method of remotely supporting a surgery assistant robot.

In recent years, surgery assistant robots have been used in surgery such as laparoscopic surgery. The necessity to provide detailed supports for the surgery assistant robots has been increasing. The specification of United States Patent Application Publication No. 2012/0330613 ("Patent Literature 1") discloses a method of monitoring a medical robot for preventive maintenance.

In remote support for surgery assistant robots by conventional methods including the method disclosed in Patent Literature 1, log data (text data) concerning an operation state of a surgery assistant robot is collected and analyzed by a remote server. When a trouble occurs in the surgery assistant robot, a person in charge in a call center receives telephone communication from a medical facility and grasps details of the trouble while viewing an analysis result of the log data of the surgery assistant robot. However, the details of the trouble cannot be grasped in some case. In that case, a serviceperson S sometimes has to visit a site (for example, an operation room where the surgery assistant robot is installed). In this case, there is a problem in terms of quickness due to a time required from the occurrence of the trouble until solution of the trouble.

One or more aspects have been devised in view of the problem described above, and aim to provide a remote support method and a remote support system that, in a site where surgery or the like using a surgery assistant robot is performed, can grasp details of a trouble in a short time and quickly perform appropriate remote support.

SUMMARY

A method according to one or more embodiments may be for remotely supporting a surgery assistant robot. The method may include: receiving at least one piece of operation information concerning an operation of the surgery assistant robot, by a server device that performs a remote support for the surgery assistant robot; and transmitting, in response to a predetermined event, at least one of a sound, an image, or a text from the server device to at least one of the surgery assistant robot or a terminal device.

A method according to one or more embodiments may be for remotely supporting a surgery assistant robot. The method may include: adjusting a frame rate of an image photographed by at least one of a surgery assistant robot or a camera that photographs an inside of a room in which the surgery assistant robot is installed; and transmitting the image, the frame rate of which is adjusted, to a server device that performs a remote support for the surgery assistant robot.

A method according to one or more embodiments may be for remotely supporting a surgery assistant robot. The method may include: processing an image photographed by at least one of a surgery assistant robot or a camera that photographs an inside of a room where the surgery assistant robot is installed, by image processing of visually obscuring identifiable information that enables a person to be identified; and transmitting an image obtained by the image processing to a server device that performs a remote support for the surgery assistant robot.

A remote support system according to one or more embodiments may include: a server device that performs a remote support for a surgery assistant robot; and a communication control device that communicates with the server device to transmit operation information concerning an operation of the surgery assistant robot to the server device and to receive information from the server device. In response to a predetermined event, the server device may perform processing of establishing bidirectional communication between at least one of the surgery assistant robot or a first terminal device used in a facility in which the surgery assistant robot is installed and a second terminal device that performs a remote support for the surgery assistant robot.

BRIEF DESCRIPTION OF DRAWINGS

FIG. 20 is a diagram illustrating an overview of a surgery assistant robot according to a fourth embodiment.

DETAILED DESCRIPTION

Figure 1:
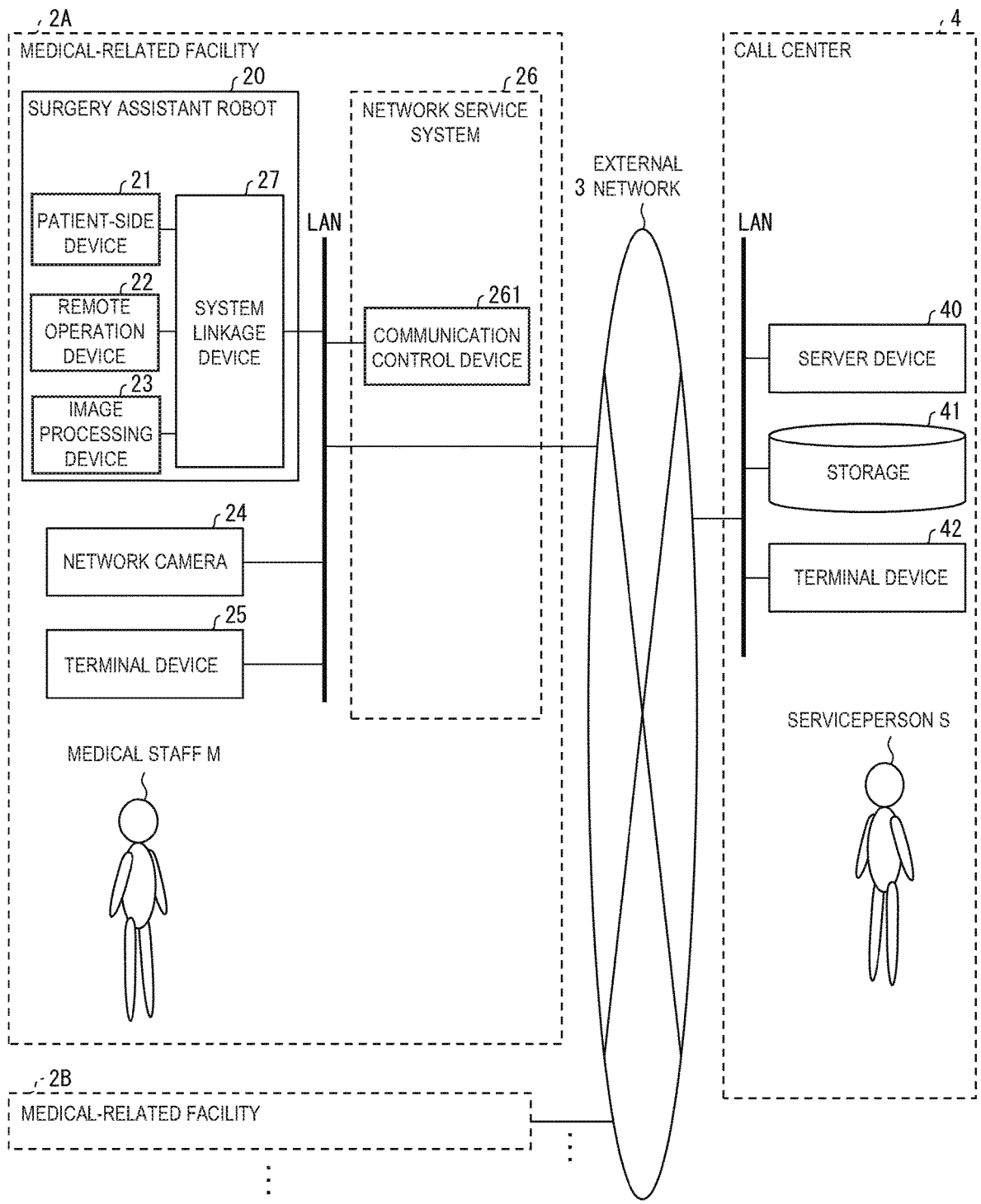
FIG. 1 is a diagram illustrating a configuration including a remote support system that realizes a remote support method according to a first embodiment.

A method of remotely supporting a surgery assistant robot according to one or more aspects includes: receiving operation information concerning the operation of a surgery assistant robot (20) by a server device (40) that performs a remote support for the surgery assistant robot (20); and, when a predetermined event is detected, transmitting at least one of a sound, an image, or a text from the server device (40) to at least one of the surgery assistant robot (20) or a terminal device (25).

A method of remotely supporting a surgery assistant robot according to one or more aspects includes: adjusting a frame rate of an image photographed by at least one of a surgery assistant robot (20) or a camera (24) that photographs the inside of a room where the surgery assistant robot (20) is installed; and transmitting the image, the frame rate of which is adjusted, to a server device (40) that performs a remote support for the surgery assistant robot (20).

A method of remotely supporting a surgery assistant robot according to one or more aspects includes: processing an image photographed by at least one of a surgery assistant robot (20) or a camera (24) that photographs the inside of a room where the surgery assistant robot (20) is installed, by image processing of visually obscuring identifying information which enables a person to be identified; and transmitting the image processed by the image processing to a server device (40) that performs a remote support for the surgery assistant robot (20).

A remote support system according to one or more aspects includes: a server device (40) that performs a remote support for a surgery assistant robot (20); and a communication control device (261) that communicates with the server device (40) in order to transmit operation information concerning the operation of the surgery assistant robot (20) to the server device (40) and receive information from the server device (40). When detecting a predetermined event, the server device (40) performs processing of establishing bidirectional communication between at least one of the surgery assistant robot (20) or a first terminal device (25) used in a facility where the surgery assistant robot (20) is installed and a second terminal device (42) that performs a remote support for the surgery assistant robot (20).

According to one or more aspects, it is possible to, in a site where surgery or the like using a surgery assistant robot is performed, grasp details of a trouble in a short time and quickly perform appropriate remote support.

First Embodiment

An embodiment is explained below with reference to FIGS. 1 to 10.

An embodiment is explained with reference to FIGS. 1 and 2. An employee (hereinafter referred to as "serviceperson S") of a call center 4 who performs a remote support job for a medical-related facility 2, which is a hospital, a medical research institute, or the like where surgery and training using a surgery assistant robot 20 are performed, quickly and appropriately remotely support doctors and medical practitioners (hereinafter referred to as "medical staff M") of the medical-related facility 2.

It is assumed that the call center 4 performs a remote support job for medical-related facilities 2. In FIG. 1, the medical-related facilities 2 are respectively described as a medical-related facility 2A, a medical-related facility 2B, and the like. When the medical-related facility 2A, the medical-related facility 2B, and the like are not distinguished, the medical-related facility 2A, the medical-related facility 2B, and the like are simply referred to as medical-related facility 2.

A major characteristic of an embodiment is that, whereas, at normal time, only communication in one direction in which at least one of operation information (explained below) of the surgery assistant robot 20 of the medical-related facility 2 and an image photographed by a network camera 24 is transmitted to a server device 40 of the call center 4 is performed, when a predetermined event (explained below) occurs, bidirectional communication becomes possible between a terminal device 25 of the call center 4 and a device (at least one of the surgery assistant robot 20, the terminal device 25, and the network camera 24) of the medical-related facility 2. In other words, a major characteristic of an embodiment is that, whereas, at normal time, only communication in one direction in which at least one of operation information (explained below) of the surgery assistant robot 20 of the medical-related facility 2 or an image photographed by a network camera 24 is transmitted to a server device 40 of the call center 4 is performed, when a predetermined event (explained below) occurs, bidirectional communication becomes possible between a terminal device 25 of the call center 4 and a device (at least one of the surgery assistant robot 20, the terminal device 25, or the network camera 24) of the medical-related facility 2.

A flow of processing until the bidirectional communication becomes possible is explained with reference to FIG. 2. First, at the normal time, operation information of the surgery assistant robot 20 is transmitted to the server device 40 via a communication control device 261 and stored in a storage 41 or a memory (S11 to S13). Similarly, an image photographed by the network camera 24 is transmitted to the server device 40 via the communication control device 261 and stored in the storage 41 (S14 to S16).

Subsequently, as an example of an event, when the surgery assistant robot 20 receives operation for requesting the bidirectional communication from the medical stall M (517), a request for establishment of the bidirectional communication is transmitted from the surgery assistant robot 20 to the server device 40 via the communication control device 261 (S18 to S19). When the request is received by the server device 40 (S20), an inquiry about possibility of the bidirectional communication is transmitted from the server device 40 to a terminal device 42 of the call center 4 (S21). The terminal device 42 outputs the received inquiry to a monitor (S22). When a response to the inquiry is input from the serviceperson S who uses the terminal device 42, the terminal device 42 transmits the response to the server device 40 (S23 to S24). When the response is a response permitting the bidirectional communication (YES in S25), the server device 40 transmits a notification to the effect that the bidirectional communication is permitted (hereinafter referred to as "permission notification") to the surgery assistant robot 20 that transmits the request (S26 to S28). In this way, the request for establishment of the bidirectional communication is transmitted (S18) and, at a stage when the permission notification is received as the response to the request (S28), the bidirectional communication is established.

After the bidirectional communication is established, data (for example, at least one of a sound, an image, and a text) input to the terminal device 42 and transmitted to the server device 40 is transmitted to the surgery assistant robot 20 via the server device 40 and the communication control device 261 (S29 to S32). In other words, data (for example, at least one of a sound, an image, or a text) input to the terminal device 42 and transmitted to the server device 40 is transmitted to the surgery assistant robot 20 via the server device 40 and the communication control device 261 (S29 to S32). Data received by the server device 40 in a period when the bidirectional communication is established is stored in the storage 41 as a log during the bidirectional communication (S33).

Figure 2:
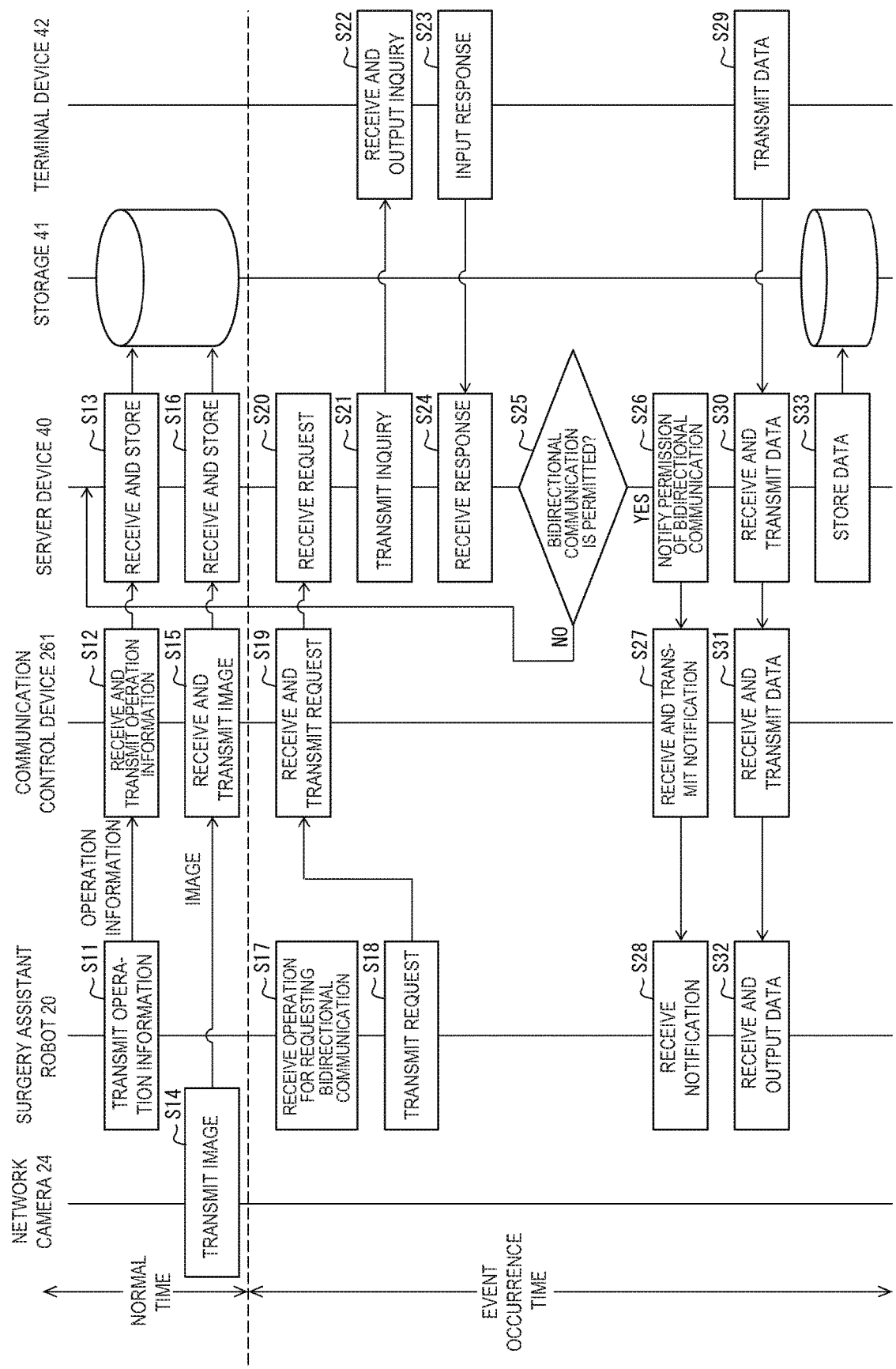
FIG. 2 is a diagram illustrating an overview of a flow of processing until bidirectional communication becomes possible in a remote support method according to a first embodiment.
Figure 3:
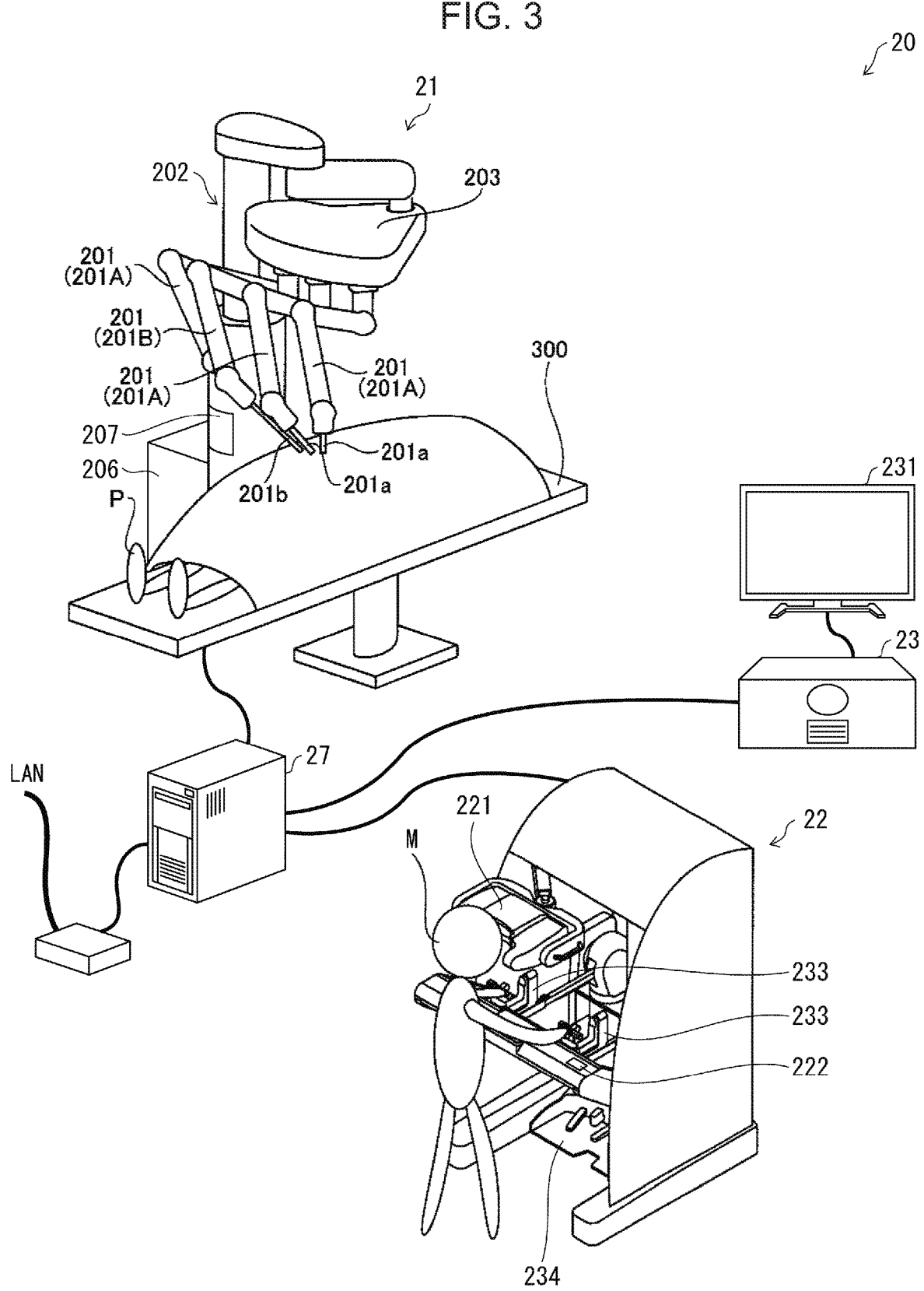
FIG. 3 is a diagram illustrating an overview of a patient-side device, a remote operation device, an image processing device, and a system linkage device configuring a surgery assistant robot.

Note that, in FIG. 2, an example is illustrated in which the surgery assistant robot 20 receives the operation for requesting the bidirectional communication and, as a result, the bidirectional communication is established between the surgery assistant robot 20 and the terminal device 42. However, when the terminal device 25 receives the operation for requesting the bidirectional communication, the bidirectional communication is established between the terminal device 25 and the terminal device 42 through the same processing.

Each of components for realizing a remote support method according to an embodiment is explained with reference to FIGS. 1 and 3 to 14.

[Medical-Related Facility 2]

A LAN (local area network) (hereinafter referred to as "intra-facility LAN") is provided in the medical-related facility 2. The intra-facility LAN is communicably connected to an external network 3. The surgery assistant robot 20, the terminal device 25, the network camera 24, and the communication control device 261 are communicably connected to the intra-facility LAN. Note that the communication control device 261 is a main device configuring a network service system 26.

[Surgery Assistant Robot 20]

The surgery assistant robot 20 is installed in an operation room (a room) of the medical-related facility 2. The surgery assistant robot 20 includes a patient-side device 21 to which medical instruments are attached, a remote operation device 22 that remotely operates the medical instruments attached to the patient-side device 21, and an image processing device 23 that processes an image photographed by an endoscope 201b, which is one of the medical instruments. The surgery assistant robot 20 includes a system linkage device 27 that mediates communication between the patient-side device 21, the remote operation device 22, and the image processing device 23 and the communication control device 261.

When an operation command for operation that should be executed by the patient-side device 21 is input to the remote operation device 22 by the medical staff M, the remote operation device 22 transmits the operation command to a controller 206 of the patient-side device 21. The controller 206 is a computer that performs operation control of the patient-side device 21. The patient-side device 21 operates, in response to the operation command transmitted from the remote operation device 22, medical instruments such as a surgical instrument and an endoscope respectively gripped by surgical manipulators 201. Consequently, minimally invasive surgery is performed.

The patient-side device 21 is arranged besides an operating table 300 on which a patient P lies. One (a first manipulator) of the surgical manipulators 201 included in the patient-side device 21 grips the endoscope 201b. The other surgical manipulators 201 (second manipulators) grip instruments 201a, which are surgical instruments. The surgical manipulators 201 that grip the instruments 201a function as instrument arms 201A. The surgical manipulator 201 that grips the endoscope 201b functions as a camera arm 201B. The instrument arms 201A and the camera arm 201B are supported by a platform 203. The surgical manipulators 201 include joints. Driving units including servomotors and position detectors such as encoders are provided in the respective joints. The surgical manipulators 201 are configured to be controlled such that medical instruments attached to the surgical manipulators 201 perform desired operations according to driving signals given via the controller 206. The platform 203 is supported by a positioner 202 placed on a floor of a room (typically an operation room) in which the surgery assistant robot 20 is installed. The positioner 202 is configured to, after being positioned with respect to the operating table 300 on which the patient P lies, move the platform 203 and the surgical manipulators 201 to positions where surgery preparation is performed. Movement of the positioner 202, the platform 203, and the surgical manipulators 201 is performed according to an input via a touch panel 207 provided in the patient-side device 21.

The instruments 201a are detachably attached to the distal end portions of the instrument arms 201A. The instruments 201a include housings attached to the instrument arms 201A and end effectors provided at the distal end portions of shafts having an elongated shape. Examples of the end effectors include gripping forceps, scissors, hooks, high-frequency knives, snare wires, clamps, and staplers. However, the end effectors are not limited to these. Various treatment instruments can be applied. The instrument arms 201A are introduced into the body of the patient P via a trocar placed on the body surface of the patient P. The end effectors of the instruments 201a are positioned near a surgical site.

The endoscope 201b is detachably attached to the distal end portion of the camera arm 201B. The camera arm 201B is introduced into the body of the patient P via the trocar placed on the body surface of the patient P. Consequently, the endoscope 201b is positioned near a surgical site and photographs the inside of the body cavity of the patient P. An image photographed by the endoscope 201b is processed by image processing by the image processing device 23 and then displayed on a monitor 221 of the remote operation device 22. The medical staff M inputs an operation command to the remote operation device 22 while viewing the image displayed on the monitor 221.

The image photographed by the endoscope 201b is processed by the image processing by the image processing device 23 and then transmitted from the system linkage device 27 to the server device 40 via the communication control device 261. As explained below, in transmitting the image to the server device 40, from the viewpoint of personal information protection, it is desirable that mask processing of masking a part of an image region can be applied by the communication control device 261 and transmission can be limited according to necessity.

The image photographed by the endoscope 201b may be processed by the image processing by the image processing device 23 and then displayed on a monitor 231 connected to the image processing device 23. Consequently, the medical staff M not operating the remote operation device 22 can also view the image photographed by the endoscope 201b.

The remote operation device 22 is a device for the medical staff M to operate the medical instruments attached to the surgical manipulators 201. An operation handle 233, an operation pedal unit 234, and the monitor 221 are provided in the remote operation device 22. The operation handle 233 is provided for the medical staff M to remotely operate the medical instruments supported by the surgical manipulators 201. The operation handle 233 is configured from a handle for right hand operated by the right hand of the medical staff M and a handle for left hand operated by the left hand of the medical staff M. For example, the medical staff M can operate the instrument 201a of the instrument arm 201A with the handle for right handle and operate the instrument 201a of another instrument arm 201A with the handle for left hand. Operation pedals are provided in the operation pedal unit 234. An operation pedal for executing a function of the instrument 201a operated by the handle for right hand, an operation pedal for executing a function of the instrument 201a operated by the handle for left hand, an operation pedal for operating the camera arm 201B with the operation handle, and the like are provided. That is, the remote operation device 22 is configured to be capable of transmitting, to the controller 206 of the patient-side device 21, an operation command for operation, which should be executed by the instrument 201a and the endoscope 201b, input by the medical staff M using the operation handle 233 and the operation pedal unit 234.

The system linkage device 27 is a computer and has functions that the computer usually has. The system linkage device 27 is communicably connected to the intra-facility LAN. The system linkage device 27 mediates communication between the patient-side device 21, the remote operation device 22, and the image processing device 23 and the communication control device 261. The system linkage device 27 is mounted with an API (application program interface). According to a request from the communication control device 261, the system linkage device 27 acquires information concerning the operation of the surgery assistant robot 20 (hereinafter referred to as "operation information") from the patient-side device 21, the remote operation device 22, and the image processing device 23 by using the API and transmits the acquired operation information to the communication control device 261. Timing when the system linkage device 27 transmits the operation information to the communication control device 261 may be immediately after the acquisition or may be after a certain degree of data amount is accumulated. Typical examples of the operation information are described in (1) to (13) below.

(1) Information concerning an occurred error (an error code, an occurrence part, an occurrence data and time, and the like)

(2) Information concerning an operation command input to the remote operation device 22

(3) Output values of various sensors attached to the remote operation device 22

(4) Output values of various sensors attached to the patient-side device 21

(5) Axis values and current values of driving units of the patient-side device 21

(6) An image photographed by the endoscope 201b.

(7) An image processed by the image processing device 23

(8) A result of an operation check performed during a system start (9) Version information of mounted software

(10) An operation mode (a surgical form/a part)

(11) Information indicating a status (a lighting state of a light emitting unit)

(12) Information concerning consumables and the number of times of operation of the consumables

(13) Information concerning charging of an electric assist device for moving the patient-side device 21 and the remote operation device 22

(1) to (13) described above are illustrations. The operation information is not limited to these.

Note that, at a stage when the predetermined event is not detected by the server device 40, in transmitting the operation information from the surgery assistant robot 20 to the server device 40, unidirectional communication is established between the surgery assistant robot 20 and the server device 40.

[Network Service System 26]

The network service system 26 provides various network services to the devices in the medical-related facility 2. Therefore, various APIs are prepared in the network service system 26.

Figure 4:
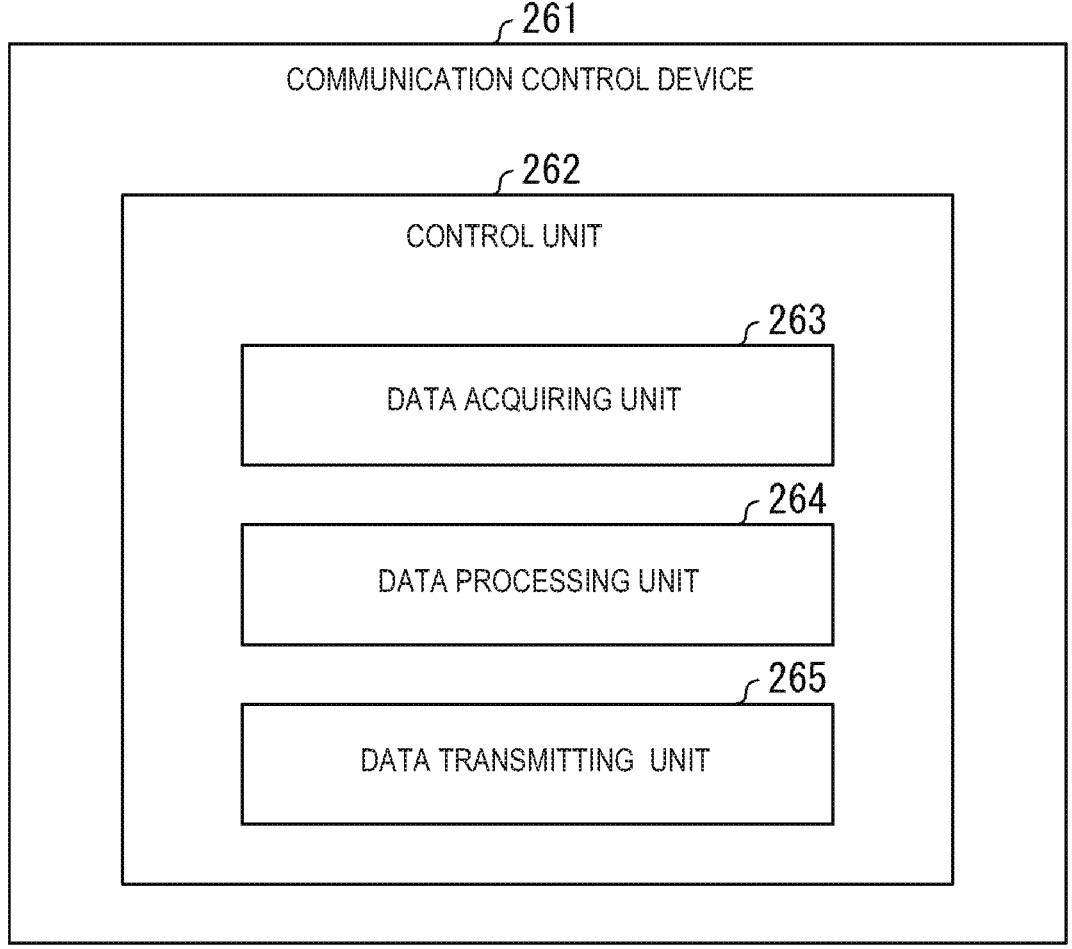
FIG. 4 is a diagram illustrating a schematic configuration of a communication control device.

The network service system 26 includes the communication control device 261. The communication control device 261 is a computer and has functions that the computer usually has. As illustrated in FIG. 4, the communication control device 261 includes a control unit 262, which is a CPU (central processing unit), and includes, as functions realized by software operating in the control unit 262, a data acquiring unit 263, a data processing unit 264, and a data transmitting unit 265.

The data acquiring unit 263 acquires operation information of the surgery assistant robot 20. This function is realized by invoking an API mounted on the system linkage device 27. The data acquiring unit 263 acquires an image photographed by the network camera 24.

Figure 5:
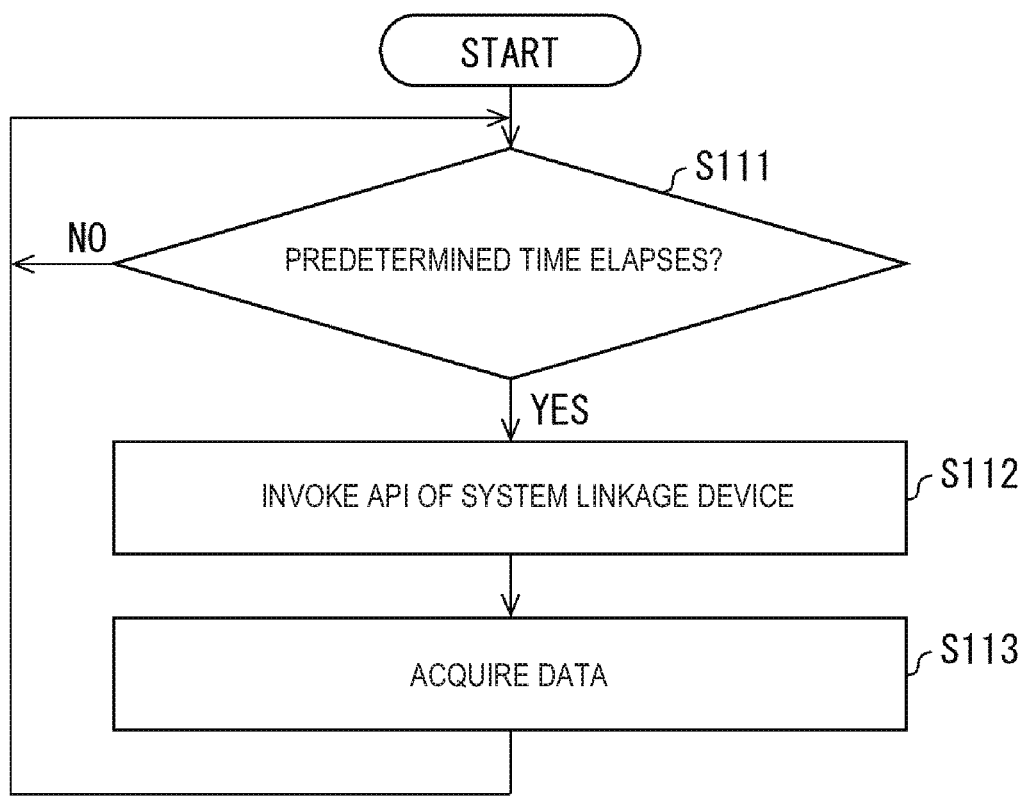
FIG. 5 is a diagram illustrating an overview of processing performed by a data acquiring unit.

An overview of processing performed by the data acquiring unit 263 is explained with reference to FIG. 5. Every time a predetermined time elapses (YES in S111), the data acquiring unit 263 invokes an API for data acquisition mounted on the system linkage device 27 (S12). The data acquiring unit 263 acquires operation information of the surgery assistant robot 20 via the API (S113).

The data processing unit 264 has functions described below.

(Function 1) Mask of Personal Information

When an image photographed by the network camera 24 and an image photographed by the endoscope 201b are transmitted via the communication control device 261, if information that can specify a person (the face of the person or the like) (hereinafter referred to as "identifiable information") is photographed, it is desirable to apply image processing of masking the identifiable information (processing of visually obscuring the identifiable information, for example, applying mosaic) from the viewpoint of personal information protection. Therefore, the data processing unit 264 inspects, sees, checks, or determines whether the identifiable information is photographed in the image to be transmitted, and processes the image by the image processing of masking the identifiable information when the identifiable information is photographed.

(Function 2) Adjustment of a Frame Rate

As a data size of a video transmitted to the server device 40 via the communication control device 261 is larger with respect to line speed of the intra-facility LAN, a more time is required for the video transmission, causing a delay. Therefore, the data processing unit 264 adjusts the number of frames per second (a frame rate) of the video to be transmitted to be small (that is, thins out frames). Specifically, the data processing unit 264 adjusts the number of frames per second to six. Note that the data processing unit 264 may monitor communication loads of the intra-facility LAN and the external network 3 and adjust the number of frames per second of the video to be small according to the communication loads.

(Function 3) Analysis of a Video and Transmission of an Analysis Result

Under the condition where a video photographed by the network camera 24 is transmitted to the server device 40 via the communication control device 261, the operation of various medical systems connected to the intra-facility LAN may be affected if a communication load is applied to the intra-facility LAN. Therefore, the data processing unit 264 analyzes a movement of a person photographed in the video to be transmitted. A transmission target to the server device 40 by the data transmitting unit 265 is only text data obtained as an analysis result. Consequently, it is possible to reduce a communication load of the intra-facility LAN compared with when the video is transmitted. "Analysis of a movement of a person" indicates that, for example, an AI (artificial intelligence) mounted on the communication control device 261 replaces a movement of a person photographed in an analysis target video with a skeleton (a bar-like model) and converts a movement of a joint of the skeleton into a numerical value.

(Function 4) Processing (Summarization) of Text Data Such as Output Values of Various Sensors The data processing unit 264 may summarize, for example, text data such as output values of various sensors acquired at an interval of one second from the surgery assistant robot 20 into an average per hour, an average per day, or the like. Consequently, in transmission to the server device 40 by the data transmitting unit 265, a transmission amount and a transmission frequency per one time are reduced. Therefore, it is possible to reduce a communication load of the external network 3.

Figure 6:
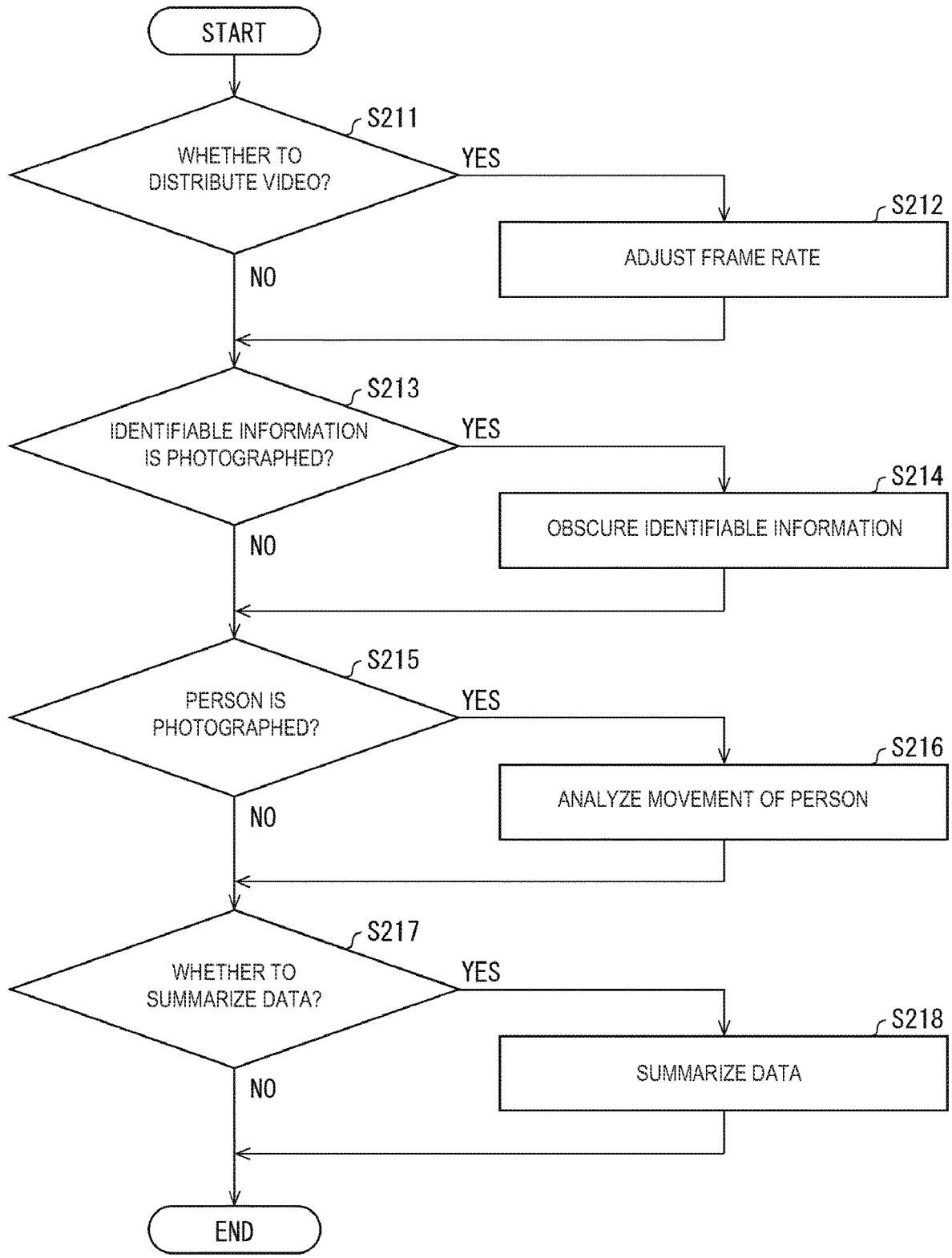
FIG. 6 is a diagram illustrating an overview of processing performed by a data processing unit.

An overview of processing performed by the data processing unit 264 is explained with reference to FIG. 6. When a video is transmitted to the server device 40 (YES in S211), the data processing unit 264 adjusts a frame rate of the video to be transmitted (S212). Subsequently, when the identifiable information is photographed in the video to be transmitted (YES in S213), the data processing unit 264 processes the video by image processing of visually obscuring the identifiable information (S214). Subsequently, when a person is photographed in the video to be transmitted (YES in S215), the data processing unit 264 analyzes a movement of the person (S216). Subsequently, when summarization of transmission target data is set (YES in S217), the data processing unit 264 summarizes the transmission target data (S218).

The data transmitting unit 265 transmits the data acquired by the data acquiring unit 263 and the data processed by the data processing unit 264 to the server device 40. Further, the data transmitting unit 265 may be configured to be able to limit the transmission of the data. Specifically, the data transmitting unit 265 does not transmit only a sound included in a video or does not transmit both of the video and the sound. Consequently, it is possible to avoid unnecessary data transmission.

Figure 7:
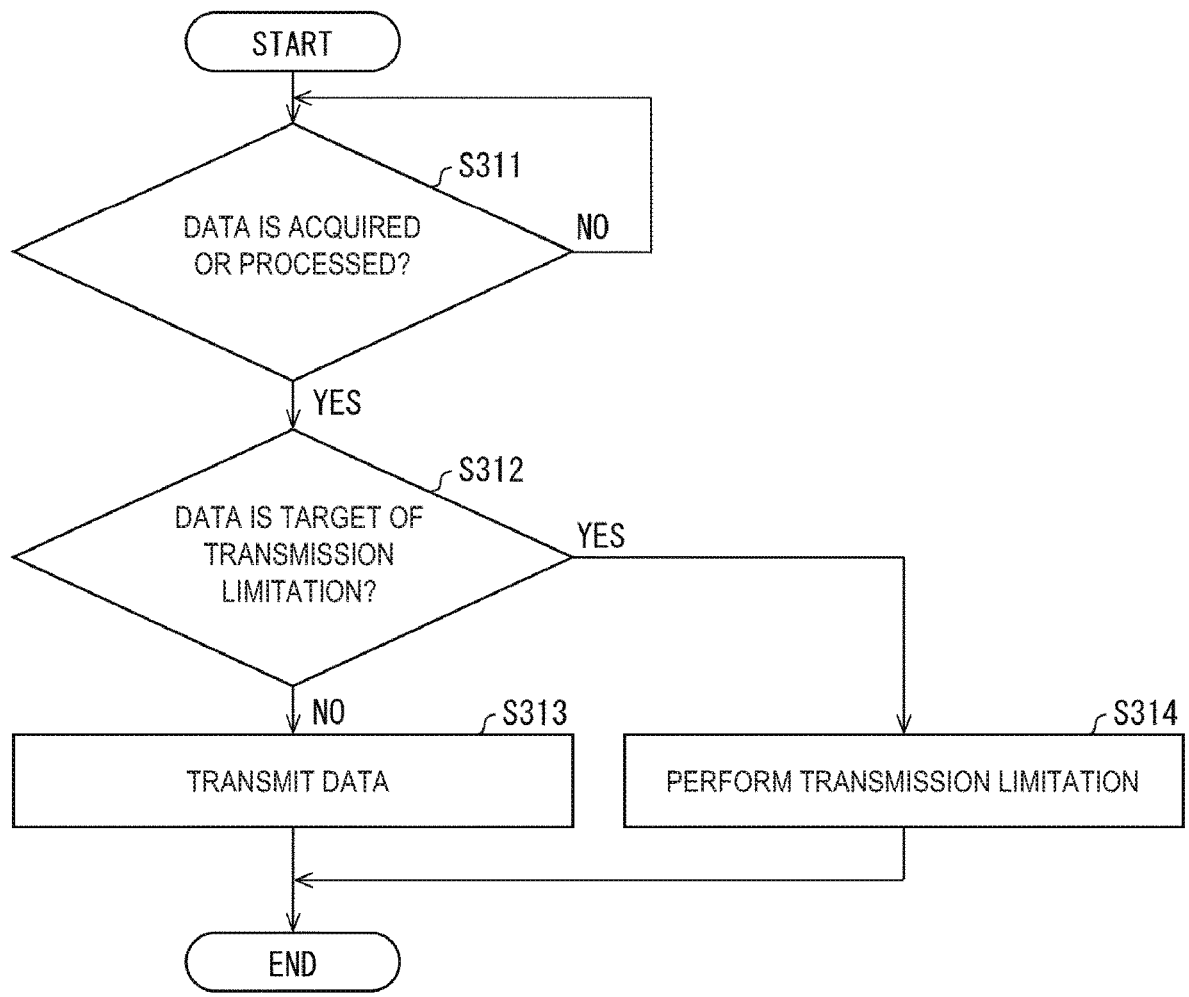
FIG. 7 is a diagram illustrating an overview of processing performed by a data transmitting unit.

An overview of processing performed by the data transmitting unit 265 is explained with reference to FIG. 7. When data is acquired by the data acquiring unit 263 or data is processed by the data processing unit 264 (YES in S311), if the data is not a target of transmission limitation (NO in S312), the data transmitting unit 265 directly transmits the data (S313). On the other hand, if the data is the target of the transmission limitation (YES in S312), the data transmitting unit 265 limits the transmission off the data (S314).

[Terminal Device 25]

The terminal device 25 is a computer terminal used by the medical staff M in the room where the surgery assistant robot 20 is installed. Typical examples of the terminal device 25 are a personal computer, a tablet terminal, a smartphone, and the like. The terminal device 25 has functions that the computer terminal usually has such as a communication function with other devices, a data input function of a keyboard and the like, a data display function of a monitor and the like, a sound input function of a microphone and the like, and a sound output function of a speaker and the like.

The terminal device 25 is communicably connected to the intra-facility LAN and accesses the network service system 26 via a Web application. For example, the terminal device 25 acquires, via the communication control device 261, data (for example, operation information of the surgery assistant robot 20) stored in the storage 41 of the call center 4 and displays the acquired data on the monitor.

The terminal device 25 is capable of receiving, from the medical staff M, operation for requesting the bidirectional communication with the terminal device 42. The terminal device 25 transmits a request corresponding to the operation to the server device 40. Examples of the operation are click of a button displayed on the monitor and a sound input to the microphone. However, the operation is not limited to these.

The terminal device 25 is capable of executing various functions for performing bidirectional communication (for example, voice call or audio call, video call, and chat) with the terminal device 42 with which the bidirectional communication with the server device 40 is established. That is, the terminal device 25 transmits data input to perform the bidirectional communication (hereinafter referred to as "communication data") to the server device 40 via the communication control device 261 in order to share the data with the terminal device 42. On the other hand, the terminal device 25 receives communication data, which is input to the terminal device 42, from the server device 40 via the communication control device 261 and outputs the communication data. Examples of the communication data are, for example, when the voice call is performed, sound, when the video call is performed, video with sound, when the chat is performed, text data, and, when data sharing using a whiteboard function is performed, graphics drawn by a paint tool. However, the communication data is not limited to these.

[Network Camera 24]

The network camera 24 is a photographing device that is installed in the room where the surgery assistant robot 20 is installed and photographs a state of the room as a video or a still image. The video is desirably a video with a sound. A photographing target may be the entire inside of the room, may be the patient-side device 21, or may be a specific medical staff M. The network camera 24 is desirably capable of optionally adjusting tilt and zoom according to an instruction from the outside.

An image photographed by the network camera 24 is transmitted to the server device 40 via the communication control device 261. As explained above, in transmitting the image to the server device 40, from the viewpoint of personal information protection, it is desirable that image processing of, for example, masking a part (for example, the face of the patient P) of an image region can be applied by the communication control device 261 and transmission can be limited according to necessity. In transmitting a video photographed by the network camera 24 to the server device 40, a frame rate of the video may be adjusted in the communication control device 261.

[Call Center 4]

The call center 4 is a facility different from the medical-related facility 2 and is a facility for performing a remote support job for the medical-related facility 2. A LAN (hereinafter referred to as "intra-call center LAN") is provided in the call center 4. The intra-call center LAN is communicably connected to the external network 3. The server device 40, the storage 41, and the terminal device 42 are communicably connected to the intra-call center LAN.

[Server Device 40]

Figure 8:
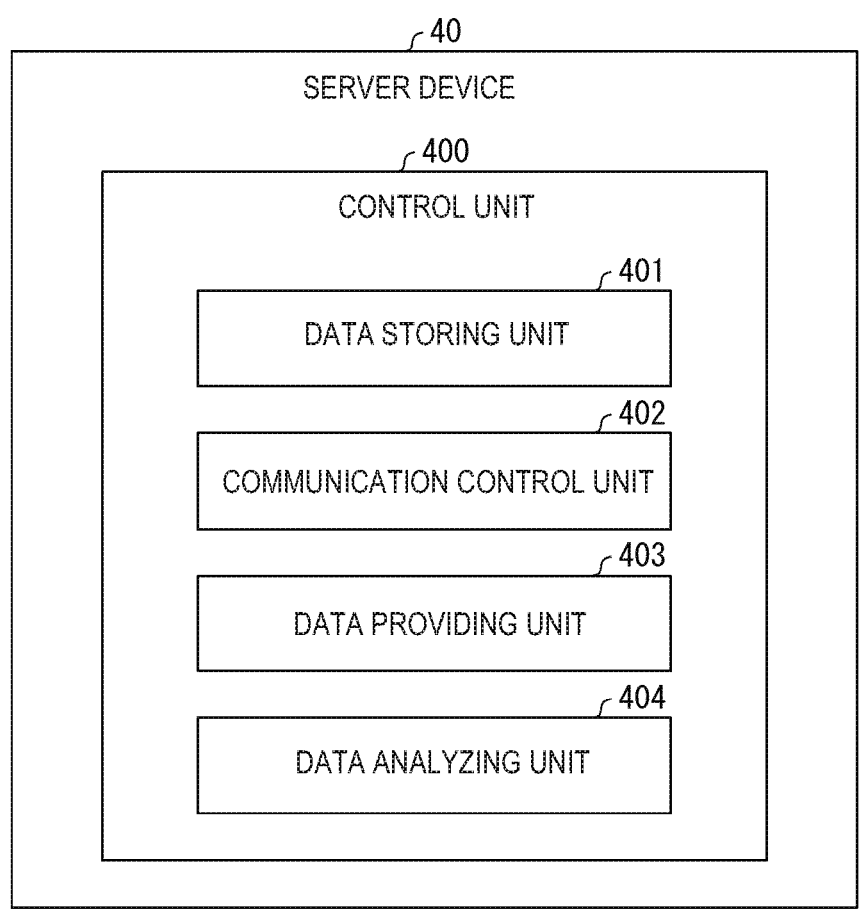
FIG. 8 is a diagram illustrating a schematic configuration of a server device.

The server device 40 is a computer and has functions that the computer usually has. The server device 40 is communicably connected to the intra-call center LAN. As illustrated in FIG. 8, the server device 40 includes a control unit 400, which is a CPU, and includes a data storing unit 401, a communication control unit 402, a data providing unit 403, and a data analyzing unit 404 as functions realized by software operating in the control unit 400.

[Data Storing Unit 401]

The data storing unit 401 stores, in the storage 41, data transmitted from the surgery assistant robot 20, the network camera 24, the terminal device 25, and the terminal device 42 to the server device 40. Typical examples of the data stored in the storage 41 by the data storing unit 401 are (1) to (5) described below.

(1) Operation information of the surgery assistant robot 20

(2) An image photographed by the endoscope 201*b*

(3) An image photographed by the network camera 24

(4) Data (various data such as a sound, an image, a text, and graphics) received from the terminal device 25

(5) Data (various data such as a sound, an image, a text, and graphics) received from the terminal device 42

In a period with which the bidirectional communication is established, the data storing unit 401 stores, in the storage 41, as a log for the bidirectional communication, data transmitted from a device with which the bidirectional communication is established to the server device 40.

Figure 9:
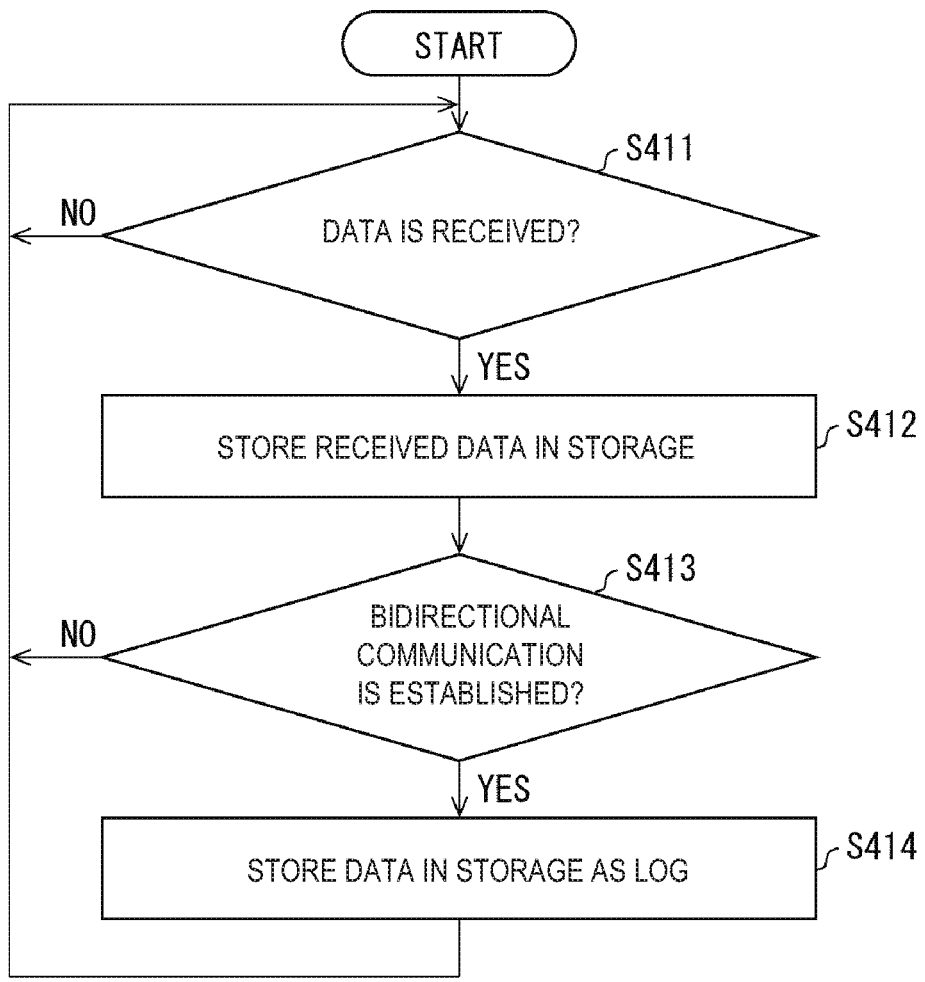
FIG. 9 is a diagram illustrating an overview of processing performed by a data storing unit.

An overview of processing performed by the data storing unit 401 is explained with reference to FIG. 9. When data is received by the server device 40 (YES in S411), the data storing unit 401 stores the received data in the storage 41 (S412). In the period with which the bidirectional communication is established (YES in S413), the data storing unit 401 stores the data in the storage 41 as a log of the bidirectional communication (S414).

[Communication Control Unit 402]

(Communication Establishment Processing)

The communication control unit 402 controls communication between the server device 40 and a device communicably connected to the server device 40. The communication control unit 402 performs processing of establishing the unidirectional communication and the bidirectional communication.

Figure 10:
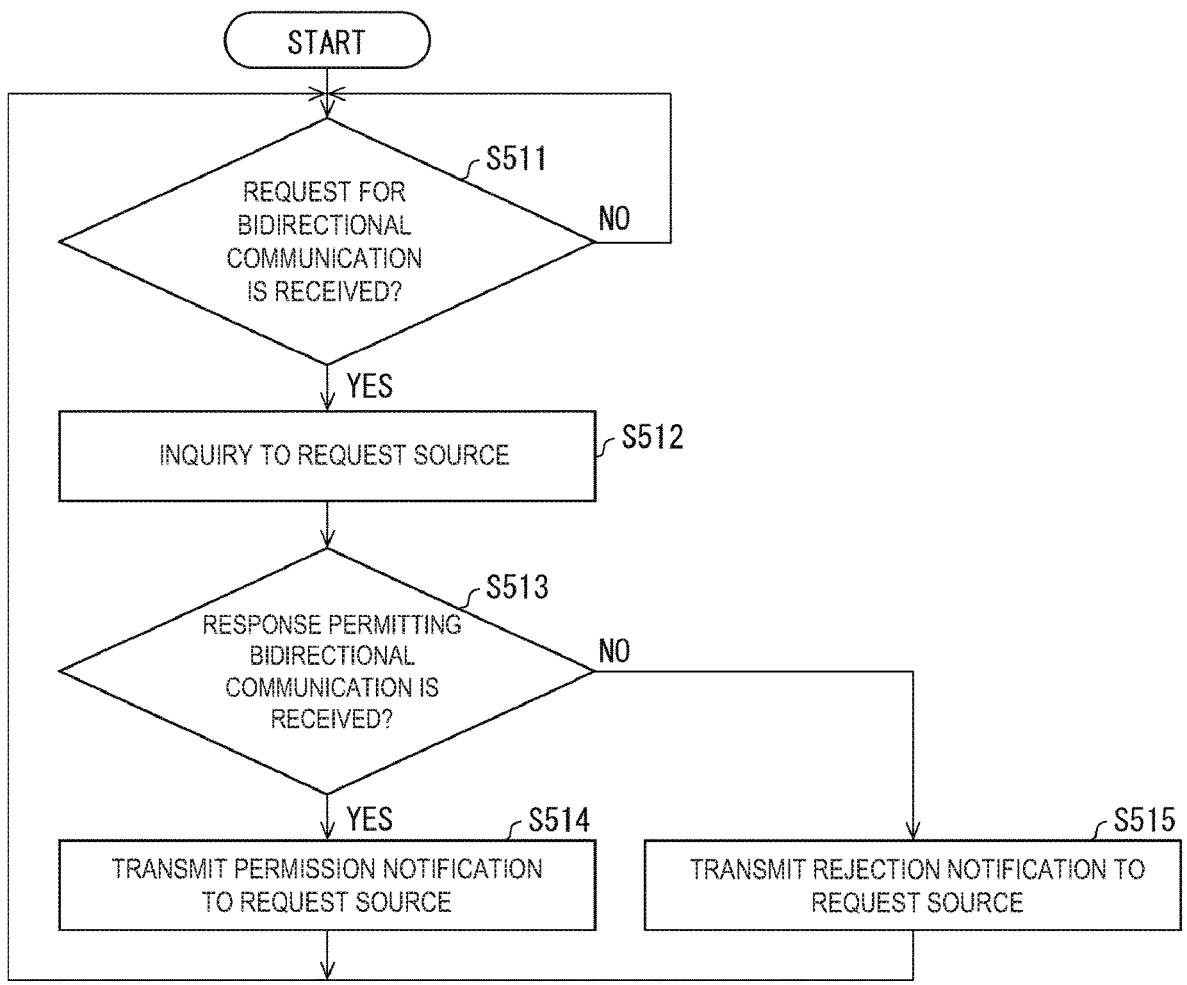
FIG. 10 is a diagram illustrating an overview of establishment processing of bidirectional communication by a communication control unit.

An overview of establishment processing of the bidirectional communication by the communication control unit 402 is explained with reference to FIG. 10. The establishment processing of the bidirectional communication by the communication control unit 402 is started by receiving a request for receiving the bidirectional communication. When receiving the request (YES in S511), the communication control unit 402 transmits an inquiry to a request destination of the bidirectional communication (S512). When a response permitting the bidirectional communication is received in response to the inquiry (YES in S513), the communication control unit 402 transmits a permission notification to the request source (S514). Consequently, the bidirectional communication is established. On the other hand, when a response rejecting the bidirectional communication is received in response to the inquiry (NO in S513), the communication control unit 402 transmits a notification to the effect that the bidirectional communication is rejected (hereinafter referred to as "rejection notification") to the request source (S515). In this case, the bidirectional communication is not established. Note that, since a publicly-known technique is used for the establishment processing of the bidirectional communication, description is omitted concerning details. The bidirectional communication is desirably full duplex communication in order to enable real-time data sharing.

Note that the communication control unit 402 is capable of establishing bidirectional communications in parallel. Specifically, the communication control unit 402 is capable of establishing the bidirectional communication between surgery assistant robots 20 set in the same medical-related facility 2 and the terminal device 42. The communication control unit 402 is also capable of establishing the bidirectional communication between the surgery assistant robots 20 set in different medical-related facilities 2 and the terminal device 42.

A trigger for the communication control unit 402 to perform the processing of establishing the bidirectional communication is detection of the predetermined event. Typical examples of the predetermined event are described in (event example 1) to (event example 5) below.

Event Example 1

A request transmitted from the surgery assistant robot 20 or the terminal device 25 according to operation for requesting the bidirectional communication is received by the server device 40.

The request is transmitted from the surgery assistant robot 20 or the terminal device 25 in which operation for requesting the bidirectional communication is performed by the medical staff M to the server device 40. When some abnormality such as a failure or an error occurs in the surgery assistant robot 20, it is highly likely that the medical staff M needs support of the serviceperson S. Therefore, it is useful to establish the bidirectional communication between the server device 40 and at least one of the surgery assistant robot 20 and the terminal device 25 and between the server device 40 and the terminal device 42. In other words, it is useful to establish the bidirectional communication between the server device 40 and at least one of the surgery assistant robot 20 or the terminal device 25 and between the server device 40 and the terminal device 42.

An example of the operation performed by the medical staff M is operation on an operation unit communicably connected to the surgery assistant robot 20 or an operation unit provided in the surgery assistant robot 20. For example, the operation performed by the medical staff M is pressing of a switch 222 provided near the remote operation device 22 (for example, at hand of the medical staff M operating the remote operation device 22) or touch on a button displayed on the touch panel 207 provided in the patient-side device 21. The former is mainly performed by the medical staff M operating the remote operation device 22. The latter is mainly performed by the medical staff M present near the patient-side device 21. The controller 206 of the surgery assistant robot 20 transmits a request for the bidirectional communication to the server device 40 in response to this operation. The communication control unit 402, which detects the request, performs processing of establishing the bidirectional communication (1) between the server device 40 and at least one of the surgery assistant robot 20 that transmits the request and the terminal device 25 and (2) between the server device 40 and the terminal device 42. In other words, the communication control unit 402, which detects the request, performs processing of establishing the bidirectional communication (1) between the server device 40 and at least one of the surgery assistant robot 20 that transmits the request or the terminal device 25 and (2) between the server device 40 and the terminal device 42.

Another example of the operation performed by the medical staff M is click of a button displayed on the monitor of the terminal device 25. A request in this case is transmitted from the terminal device 25 to the server device 40. The communication control unit 402, which detects the request, performs processing of establishing the bidirectional communication (1) between the server device 40 and at least one of the terminal device 25 that transmits the request and the surgery assistant robot 20 and (2) between the server device 40 and the terminal device 42. In other words, the communication control unit 402, which detects the request, performs processing of establishing the bidirectional communication (1) between the server device 40 and at least one of the terminal device 25 that transmits the request or the surgery assistant robot 20 and (2) between the server device 40 and the terminal device 42.

Still another example of the operation performed by the medical staff M is input of a sound or a voice requesting establishment of the bidirectional communication to the surgery assistant robot 20 or the terminal device 25.

Event Example 2

A request transmitted from the terminal device 42 according to operation for requesting the bidirectional communication is received by the server device 40.

This request is transmitted from the terminal device 42 in which operation for requesting the bidirectional communication is performed by the serviceperson S to the server device 40. This operation is performed when the serviceperson S, who detects an abnormality or the like of the surgery assistant robot 20, determines that the serviceperson S should support the medical staff M. For example, when an abnormal value indicating an error, a failure, or the like is included in the operation information of the surgery assistant robot 20, the medical staff M is likely to need support of the serviceperson S. Therefore, it is useful to establish the bidirectional communication between the server device 40 and the terminal device 42 and between the server device 40 and at least one of the surgery assistant robot 20 and the terminal device 25. In other words, it is useful to establish the bidirectional communication between the server device 40 and the terminal device 42 and between the server device 40 and at least one of the surgery assistant robot 20 or the terminal device 25.

Typical examples of the abnormal value included in the operation information are an axis value and a current value from which it is surmised that the instrument arm 201A and the camera arm 201B are in a state in which the instrument arm 201A and the camera arm 201B interfere with each other and do not move and an error code indicating that restart of the surgery assistant robot 20 is necessary.

An example of the operation performed by the serviceperson S is designation of the surgery assistant robot 20 that should be remotely operated in the terminal device 42. The request is transmitted from the terminal device 42 to the server device 40. The communication control unit 402, which detects the request, performs processing of establishing the bidirectional communication (1) between the server device 40 and the terminal device 42 that transmits the request and (2) between the server device 40 and at least one of the designated surgery assistant robot 20 and the terminal device 25. In other words, the communication control unit 402, which detects the request, performs processing of establishing the bidirectional communication (1) between the server device 40 and the terminal device 42 that transmits the request and (2) between the server device 40 and at least one of the designated surgery assistant robot 20 or the terminal device 25.

Another example of the operation performed by the serviceperson S is designation of the terminal device 25 of the medical staff M who should be supported in the terminal device 42. In this case as well, the request is transmitted from the terminal device 42 to the server device 40. The communication control unit 402, which detects the request, performs processing of establishing the bidirectional communication (1) between the server device 40 and the terminal device 42 that transmits the request and (2) between the server device 40 and at least one of the designated terminal device 25 and the surgery assistant robot 20. In other words, the communication control unit 402, which detects the request, performs processing of establishing the bidirectional communication (1) between the server device 40 and the terminal device 42 that transmits the request and (2) between the server device 40 and at least one of the designated terminal device 25 or the surgery assistant robot 20.

Event Example 3

Detection of the abnormal value included in the operation information.

As explained above, typical examples of the abnormal value included in the operation information are an axis value and a current value from which it is surmised that the instrument arm 201A and the camera arm 201B are in a state in which the instrument arm 201A and the camera arm 201B interfere with each other and do not move and an error code indicating that restart of the surgery assistant robot 20 is necessary. In this case, the medical staff M is likely to need support of the serviceperson S. Accordingly, the serviceperson S is desirably able to quickly perform data sharing with the medical staff M or remote operation of the surgery assistant robot 20.

In this case, the communication control unit 402 performs processing of establishing the bidirectional communication (1) between the server device 40 and at least one of the terminal device 25 and the surgery assistant robot 20 provided in the same medical-related facility 2 as the medical-related facility 2 in which the network camera 24 is provided and (2) between the server device 40 and the terminal device 42. In other words, the communication control unit 402 performs processing of establishing the bidirectional communication (1) between the server device 40 and at least one of the terminal device 25 or the surgery assistant robot 20 provided in the same medical-related facility 2 as the medical-related facility 2 in which the network camera 24 is provided and (2) between the server device 40 and the terminal device 42.

Event Example 4

Detection of an abnormal situation (specifically, detection of unusual behavior of the medial staff M) based on an image analysis of a video photographed by the network camera 24.

The unusual behavior is, for example, behavior different from normal time (for example, suddenly busily moving around) and behavior of operating an unusual device (for example, behavior of operating a specific telephone). In this case, the serviceperson S is desirably able to quickly perform data sharing with the medical staff M or remote operation of the surgery assistant robot 20.

In this case, the communication control unit 402 performs processing of establishing the bidirectional communication (1) between the server device 40 and at least one of the terminal device 25 and the surgery assistant robot 20 provided in the same medical-related facility 2 as the medical-related facility 2 in which the network camera 24 is provided and (2) between the server device 40 and the terminal device 42. In other words, the communication control unit 402 performs processing of establishing the bidirectional communication (1) between the server device 40 and at least one of the terminal device 25 or the surgery assistant robot 20 provided in the same medical-related facility 2 as the medical-related facility 2 in which the network camera 24 is provided and (2) between the server device 40 and the terminal device 42.

Event 5

Detection of an abnormal situation (specifically, detection of a specific phrase or volume or frequency exceeding a threshold) based on a sound analysis of a video photographed by the network camera 24.

When a phrase seeking help of the call center 4 is detected or volume or frequency exceeding a threshold is detected, it is highly likely that utterance is performed because of occurrence of some problem and it is highly likely that the medical staff M needs support of the serviceperson S. Accordingly, the serviceperson S is desirably able to quickly perform data sharing with the medical staff M and remote operation of the surgery assistant robot 20.

In this case, the communication control unit 402 performs processing of establishing the bidirectional communication (1) between the server device 40 and at least one of the terminal device 25 and the surgery assistant robot 20 provided in the same medical-related facility 2 as the medical-related facility 2 in which the network camera 24 is provided and (2) between the server device 40 and the terminal device 42. In other words, the communication control unit 402 performs processing of establishing the bidirectional communication (1) between the server device 40 and at least one of the terminal device 25 or the surgery assistant robot 20 provided in the same medical-related facility 2 as the medical-related facility 2 in which the network camera 24 is provided and (2) between the server device 40 and the terminal device 42.

(Data Transmission Processing)

The communication control unit 402 transmits, to a partner device with which the bidirectional communication is established, various data transmitted from the device with which the bidirectional communication is established to the server device 40. Transmission examples are described in (transmission example 1) to (transmission example 7) below.

Transmission Example 1

In a condition in which the bidirectional communication is established, the communication control unit 402 transmits data (at least one of a sound, an image, and a text) input to one of at least one of the surgery assistant robot 20 and the terminal device 25 and the terminal device 42 and transmitted to the server device 40 to the other of the at least one of the surgery assistant robot 20 and the terminal device 25 and the terminal device 42. In other words, in a condition in which the bidirectional communication is established, the communication control unit 402 transmits data (at least one of a sound, an image, or a text) input to one of at least one of the surgery assistant robot 20 or the terminal device 25 and the terminal device 42 and transmitted to the server device 40 to the other of the at least one of the surgery assistant robot 20 or the terminal device 25 and the terminal device 42. Consequently, it is possible to quickly share advices and instructions between the medical staff M and the serviceperson S. Therefore, effects equivalent to effects obtained when the serviceperson S is present and supports the medical staff M in the site can be obtained. Note that, if the data providing unit 403 is always transmitting operation information of the surgery assistant robot 20 to the terminal device 42, the serviceperson S can estimate, based on operation information provided before the bidirectional communication is established, a cause of a trouble and a method of coping with the trouble. Therefore, the serviceperson S can quickly and appropriately support the medical staff M immediately after the bidirectional communication is established.

Figure 11:
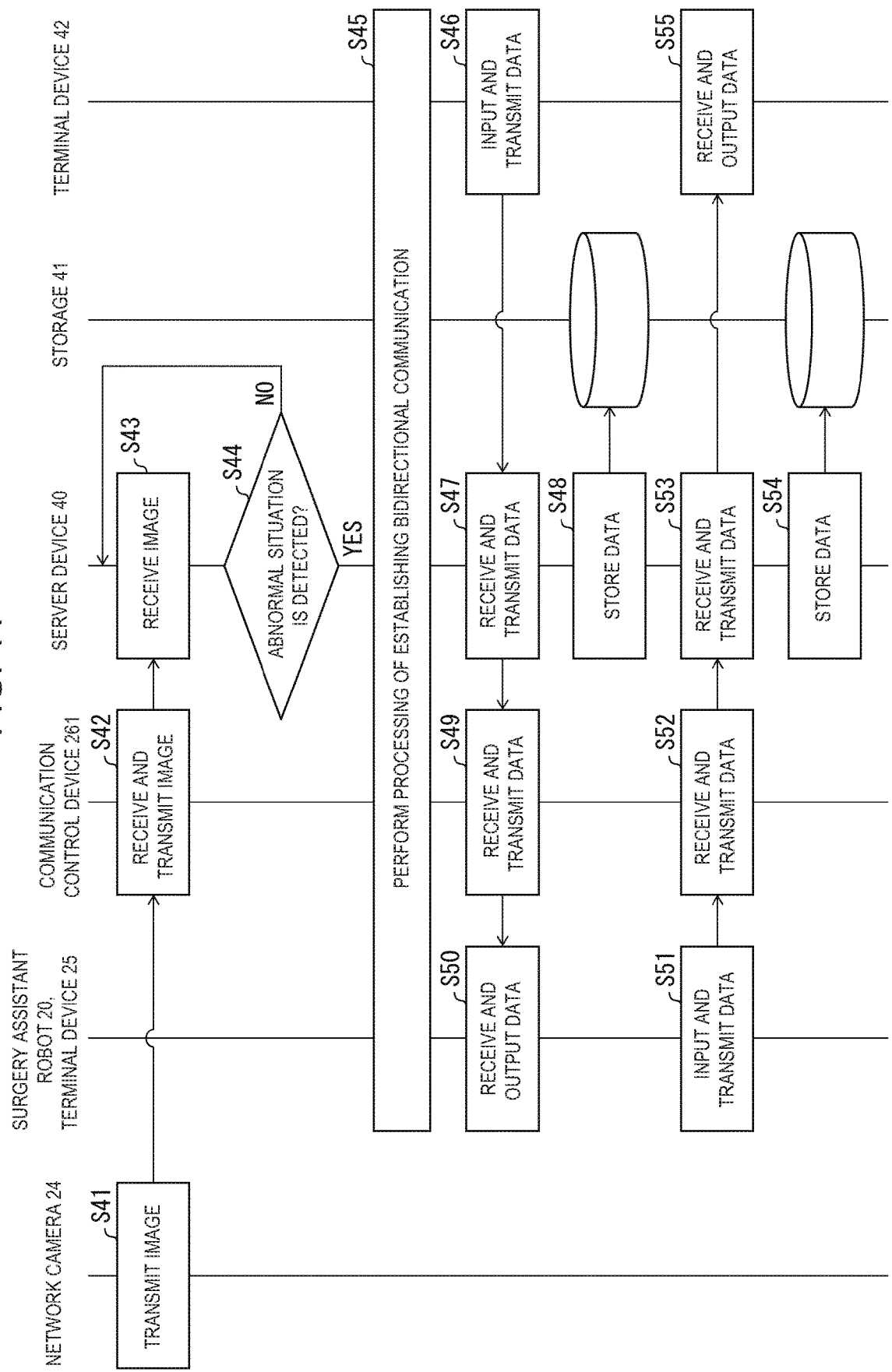
FIG. 11 is a diagram illustrating an example of a flow of processing in which data input to a terminal device in which bidirectional communication is established by detecting an abnormal situation in an image photographed by a network camera is transmitted.

As an example, an example of a flow of processing with which the bidirectional communication is established by the event example 3 or the event example 4 explained above and the transmission example 1 is performed is explained with reference to FIG. 11. An image photographed by the network camera 24 is transmitted to the server device 40 via the communication control device 261 (S41 and S42). When the server device 40 receives the image (S43) and the communication control unit 402 detects an abnormal situation (YES in S44), the establishment processing of the bidirectional communication is performed between the server device 40 and at least one of the surgery assistant robot 20 and the terminal device 25 and between the server device 40 and the terminal device 42 (S45). In other words, the establishment processing of the bidirectional communication is performed between the server device 40 and at least one of the surgery assistant robot 20 or the terminal device 25 and between the server device 40 and the terminal device 42 (S45). Since the establishment processing of the bidirectional communication is as explained above, details of the establishment processing are omitted. After the bidirectional communication is established, data input to the terminal device 42 and transmitted to the server device 40 is transmitted from the communication control unit 402 to at least one of the surgery assistant robot 20 and the terminal device 25 (S46 to S47). In other words, data input to the terminal device 42 and transmitted to the server device 40 is transmitted from the communication control unit 402 to at least one of the surgery assistant robot 20 or the terminal device 25 (S46 to S47). At this time, the data storing unit 401 stores transmission data in the storage 41 as a log of the bidirectional communication (S48). At least one of the surgery assistant robot 20 and the terminal device 25, which receive the data via the communication control device 261, outputs the data (S49 to S50). In other words, at least one of the surgery assistant robot 20 or the terminal device 25, which receive the data via the communication control device 261, outputs the data (S49 to S50). Similarly, data input to the surgery assistant robot 20 or the terminal device 25 and transmitted to the server device 40 is transmitted from the communication control unit 402 to the terminal device 42 (S51 to S53). The terminal device 42 outputs the received data (S55). At this time, the data storing unit 401 stores transmission data in the storage 41 as a log of the bidirectional communication (S54). Note that, when the bidirectional communication is full duplex communication, S46 to S50 and S51 to S55 can be performed in parallel.

Transmission Example 2

When the bidirectional communication is established, the communication control unit 402 desirably transmits, to at least the terminal device 42, an image photographed by the network camera 24 and received by the server device 40. The terminal device 42 displays the transmitted image on the monitor. Consequently, the medical staff M and the serviceperson S can visually share a present state of the operating room equivalently to or better than when the serviceperson S is present in the site. Therefore, the serviceperson S can appropriately support the medical staff M. Note that the terminal device 25 may be added as a transmission destination of the image.

Transmission Example 3

When the bidirectional communication is established, the communication control unit 402 desirably transmits, to at least the terminal device 42, an image photographed by the endoscope 201b and received by the server device 40. The terminal device 42 displays the transmitted image on the monitor. Consequently, the medical staff M and the serviceperson S can visually share a state in the body cavity of the patient P equivalently to or better than when the serviceperson S is present in the site. Therefore, the serviceperson S can appropriately support the medical staff M. Note that the terminal device 25 may be added as a transmission destination of the image.

Transmission Example 4

The transmission explained in the transmission example 2 and the transmission explained in the transmission example 3 are desirably simultaneously performed. That is, it is desirable to transmit, to at least the terminal device 42, an image photographed by the network camera 24 and received by the server device 40 and an image photographed by the endoscope 201b and received by the server device 40. The terminal device 42 simultaneously displays both the transmitted images on the monitor. Consequently, the serviceperson S can confirm a present state of the operating room and a state in the body cavity of the patient P. Therefore, the serviceperson S can appropriately support the medical staff M. Note that the terminal device 25 may be added as a transmission destination of the image.

Transmission Example 5

It is assumed that the communication control unit 402 transmits an image (at least one of an image photographed by the network camera 24 and an image photographed by the endoscope 201b) to the terminal device 42 with which the bidirectional communication is established and the image is displayed on a monitor of the terminal device 42. In other words, it is assumed that the communication control unit 402 transmits an image (at least one of an image photographed by the network camera 24 or an image photographed by the endoscope 201b) to the terminal device 42 with which the bidirectional communication is established and the image is displayed on a monitor of the terminal device 42. Further, it is assumed that the communication control unit 402 also transmits the image to at least one of the surgery assistant robot 20 and the terminal device 25 with which the bidirectional communication is established and the image is displayed on a monitor included in the surgery assistant robot 20 (the touch panel 207 provided in the patient-side device 21 and the monitor 231 connected to the image processing device 23) or the monitor of the terminal device 42. In other words, it is assumed that the communication control unit 402 also transmits the image to at least one of the surgery assistant robot 20 or the terminal device 25 with which the bidirectional communication is established and the image is displayed on a monitor included in the surgery assistant robot 20 (the touch panel 207 provided in the patient-side device 21 and the monitor 231 connected to the image processing device 23) or the monitor of the terminal device 42. In this case, data (for example, graphics drawn by a paint tool in a display region of the image) to be superimposed and displayed on the image is input to the terminal device 42, the data is transmitted to the server device 40. The communication control unit 402 transmits the data to at least one of the surgery assistant robot 20 and the terminal device 25 with which the bidirectional communication is established. In other words, the communication control unit 402 transmits the data to at least one of the surgery assistant robot 20 or the terminal device 25 with which the bidirectional communication is established. The surgery assistant robot 20, which receives the data, superimposes and displays the data on the image transmitted from the communication control unit 402 and displayed on the monitor. Similarly, the terminal device 25, which receives the data, superimposes and displays the data on the image transmitted from the communication control unit 402 and displayed on the monitor. Consequently, both of the medical staff M and the serviceperson S can share a processed image, the image on which the data is superimposed and displayed. Therefore, for example, by drawing marking in a noticeable part in the image in the terminal device 42, both of the medical staff M and the serviceperson S can easily share the noticeable part.

Figure 12:
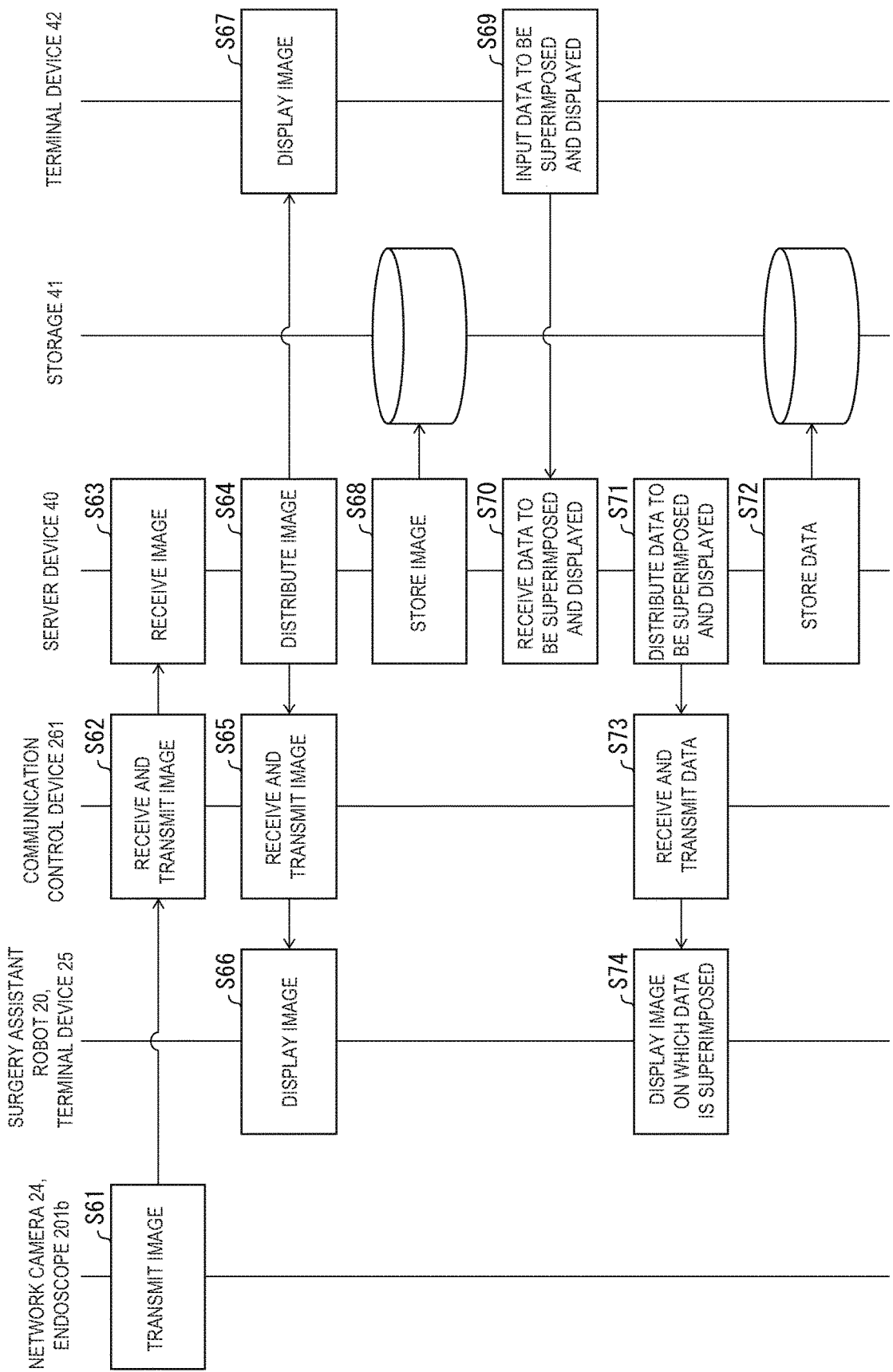
FIG. 12 is a diagram illustrating an example of a flow of processing in which transmission of an image is performed in a state in which bidirectional communication is established between terminal devices.

As an example, an example of a flow of processing in which the transmission examples 2 to 5 are performed in a state with which the bidirectional communication is established between the server device 40 and the surgery assistant robot 20 and the terminal device 25 and between the server device 40 and the terminal device 42 is explained with reference to FIG. 12. First, an image photographed by at least one of the network camera 24 and the endoscope 201b is transmitted to the server device 40 via the communication control device 261 (S61 and S62). In other words, an image photographed by at least one of the network camera 24 or the endoscope 201b is transmitted to the server device 40 via the communication control device 261 (S61 and S62). When the server device 40 receives the image (S63), the communication control unit 402 transmits the image to the terminal device 42 with which the bidirectional communication is established and transmits the image to the surgery assistant robot 20 and the terminal device 25 (S64). The surgery assistant robot 20 and the terminal device 25 display the image transmitted via the communication control device 261 on the monitors (S65 and A66). Similarly, the terminal device 42 displays the image on the monitor (S67). Consequently, the image is displayed on the monitors of the surgery assistant robot 20, the terminal device 25, and the terminal device 42. At this time, the data storing unit 401 stores the transmitted image in the storage 41 as a log of the bidirectional communication (S68). Subsequently, when data to be superimposed and displayed on the image is input by the serviceperson S of the terminal device 42 (S69), the data is received by the server device 40 (S70). The communication control unit 402 transmits the data to the surgery assistant robot 20 and the terminal device 25 via the communication control device 261 (S71 and S73). The surgery assistant robot 20 and the terminal device 25, which receive the data, display, on the monitors, the processed image on which the data is superimposed and displayed (S74). The data storing unit 401 stores the processed image on which the data is superimposed and displayed in the storage 41 as a log of the bidirectional communication (S72).

Transmission Example 6

The communication control unit 402 transmits, to the surgery assistant robot 20, an operation command and a warning output instruction for the surgery assistant robot 20 input to the terminal device 42 and transmitted to the server device 40. Consequently, the serviceperson S can quickly remotely operate the surgery assistant robot 20.

Transmission Example 7

When data such as a sound, an image, and a text can be input to the surgery assistant robot 20, the communication control unit 402 may transmit, to the terminal device 42, the data input to the surgery assistant robot 20 and transmitted to the server device 40. Conversely, when data such as a sound, an image, and a text can be output in the surgery assistant robot 20, the communication control unit 402 may transmit, to the surgery assistant robot 20, the data input to the terminal device 42 and transmitted to the server device 40. Consequently, communication between the medical staff M and the serviceperson S is possible even if the terminal device 25 is not used.

[Data Providing Unit 403]

The data providing unit 403 transmits data corresponding to a request from the terminal device 25 to the terminal device 25 at the request source. Similarly, the data providing unit 403 provides data corresponding to a request from the terminal device 42 to the terminal device 42 at the request source. Therefore, various APIs are prepared in the data providing unit 403. Typical examples of the data provided to the terminal device 25 and the terminal device 42 are data stored in the storage 41, in particular, operation information of the surgery assistant robot 20, an image photographed by the network camera 24, and an image photographed by the endoscope 201b.

Note that the data providing unit 403 desirably always transmits the operation information received from the surgery assistant robot 20 to the terminal device 42. Consequently, the serviceperson S can always monitor a state of the surgery assistant robot 20 in the terminal device 42. Therefore, the serviceperson S can confirm, beforehand, a cause of a trouble and a method of coping with the trouble based on the operation information of the surgery assistant robot 20 before the bidirectional communication is established. Therefore, the serviceperson S can quickly and appropriately support the medical staff M immediately after bidirectional communication with the medical staff M is started.

When an error is included in the data to be provided, the data providing unit 403 transmits a notification concerning the error to the terminal device 25 or the terminal device 42 at the request source. A method of coping with the error may be included in the notification concerning the error. The method of coping with the error is, for example, a hyper link with a link destination set in a relevant part in an electronic manual and data obtained by dynamically summarizing only necessary information among accumulated information concerning the method of coping with the error. However, the method of coping with the error is not limited to these.

Note that the data providing unit 403 may statistically analyze, with the data analyzing unit 404, the data to be provided and then transmit the data or may organize a display form of the data to be provided and then transmit the data.

Figure 13:
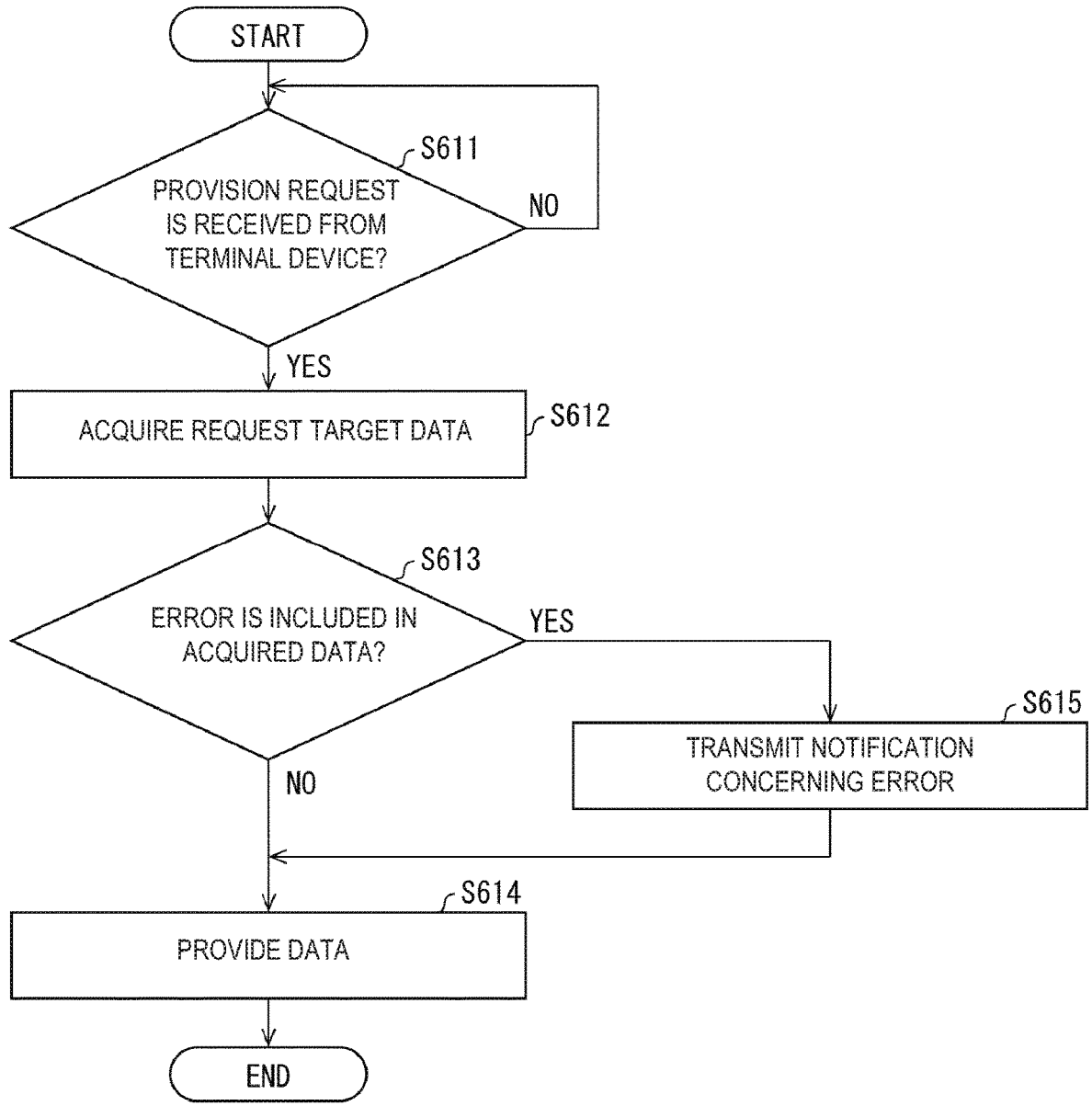
FIG. 13 is a diagram illustrating an overview of processing performed by a data providing unit.

An overview of processing performed by the data providing unit 403 is explained with reference to FIG. 13. When a request for provision of data is received from the terminal device 25 or the terminal device 42 (YES in S611), the data providing unit 403 acquires request target data from the storage 41 (S612). If an error is not included in the acquired data (NO in S613), the data providing unit 403 directly provides the data to the request source (S614). On the other hand, if an error is included in the acquired data (YES in S613), the data providing unit 403 transmits a notification concerning the error to the request source (S615). In FIG. 13, the data providing unit 403 provides the data to the request source following S615 (S614). However, the data provision to the request source may be omitted according to content of the error.

[Data Analyzing Unit 404]

The data analyzing unit 404 performs an analysis of various data according to a request from the terminal device 25 or the terminal device 42 and transmits an analysis result to the request source. Therefore, various APIs for analysis are prepared in the data providing unit 403. A typical example of analysis target data is data (typically, operation information of the surgery assistant robot 20) stored in the storage 41.

Figure 14:
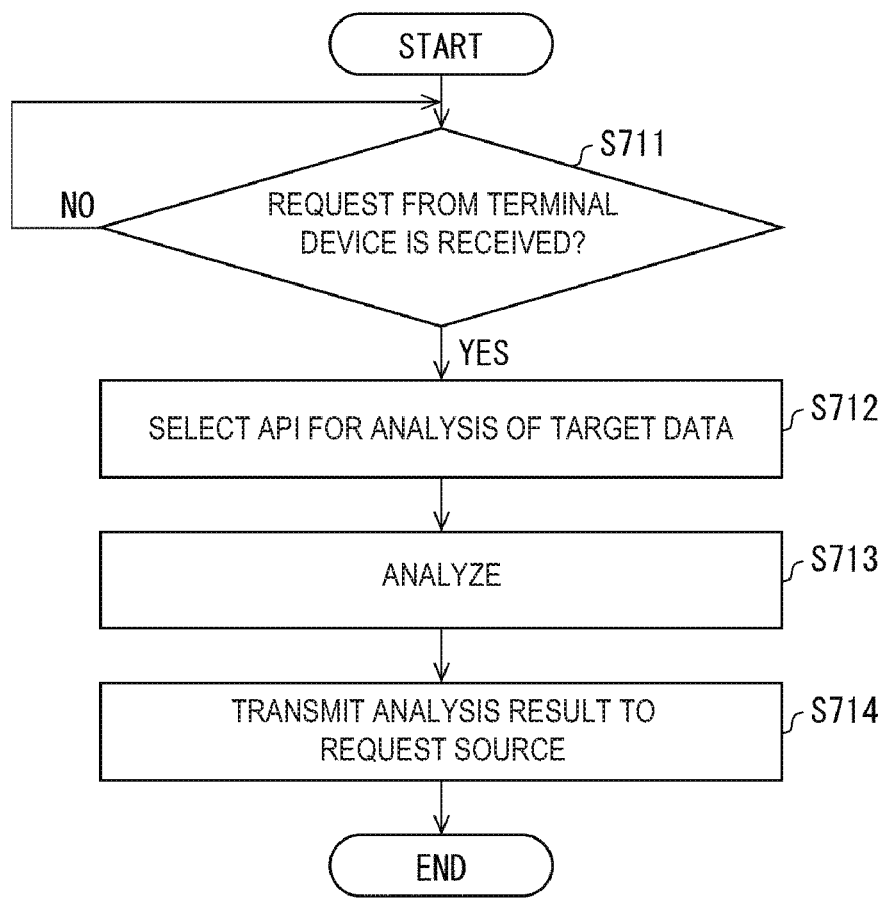
FIG. 14 is a diagram illustrating an overview of processing performed by a data analyzing unit.

An overview of processing performed by the data analyzing unit 404 is explained with reference to FIG. 14. When an analysis request for data is received from the terminal device 25 or the terminal device 42 (YES in S711), the data analyzing unit 404 selects an API for analyzing target data (S712) and executes an analysis (S713). The data analyzing unit 404 transmits an analysis result to the request source (S714).

[Terminal Device 42]

The terminal device 42 is a computer terminal used in the call center 4 by the serviceperson S of the call center 4. Typical examples of the terminal device 42 are a personal computer, a tablet terminal, a smartphone, and the like. The terminal device 42 is communicably connected to the server device 40 via a LAN in the call center 4.

Note that the terminal device 42 has functions that the computer terminal usually has such as a communication function with other devices, a data input function of a keyboard and the like, a data display function of a monitor and the like, a sound input function of a microphone and the like, and a sound output function of a speaker and the like.

The terminal device 42 acquires data (typically, the operation information of the surgery assistant robot 20) stored in the storage 41 via the server device 40 and displays the acquired data on the monitor.

The terminal device 42 is capable of receiving, from the serviceperson S, operation for requesting the bidirectional communication with the surgery assistant robot 20 or the terminal device 25. The terminal device 42 transmits a request corresponding to the operation to the server device 40. Examples of the operation are click of a button displayed on the monitor and a sound input to the microphone. However, the operation is not limited to these.

The terminal device 42 is capable of executing various functions for performing bidirectional communication and data sharing with the terminal device 25 with which the bidirectional communication is established. That is, the terminal device 42 transmits communication data to the server device 40 in order to share the communication data with the terminal device 25. On the other hand, the terminal device 42 receives, from the server device 40, communication data input to the terminal device 25

The terminal device 42 is capable of receiving a command to the surgery assistant robot 20 with which the bidirectional communication is established. Examples of the command are a warning output command from the surgery assistant robot 20 and an operation command for remotely operating the surgery assistant robot 20.

The terminal device 42 can acquire a screen displayed on the monitor 221 of the remote operation device 22 of the surgery assistant robot 20 with which the bidirectional communication is established and display the screen on the monitor of the terminal device 42.

When the surgery assistant robot 20 includes an output unit that outputs data such as a sound, an image, and a text, the terminal device 42 may transmit, through the server device 40, the data to the surgery assistant robot 20 with which the bidirectional communication is established.

[Storage 41]

The storage 41 is a device that stores various data and is, for example, a magnetic disk such as a hard disk.

Screen Example

Figure 15:
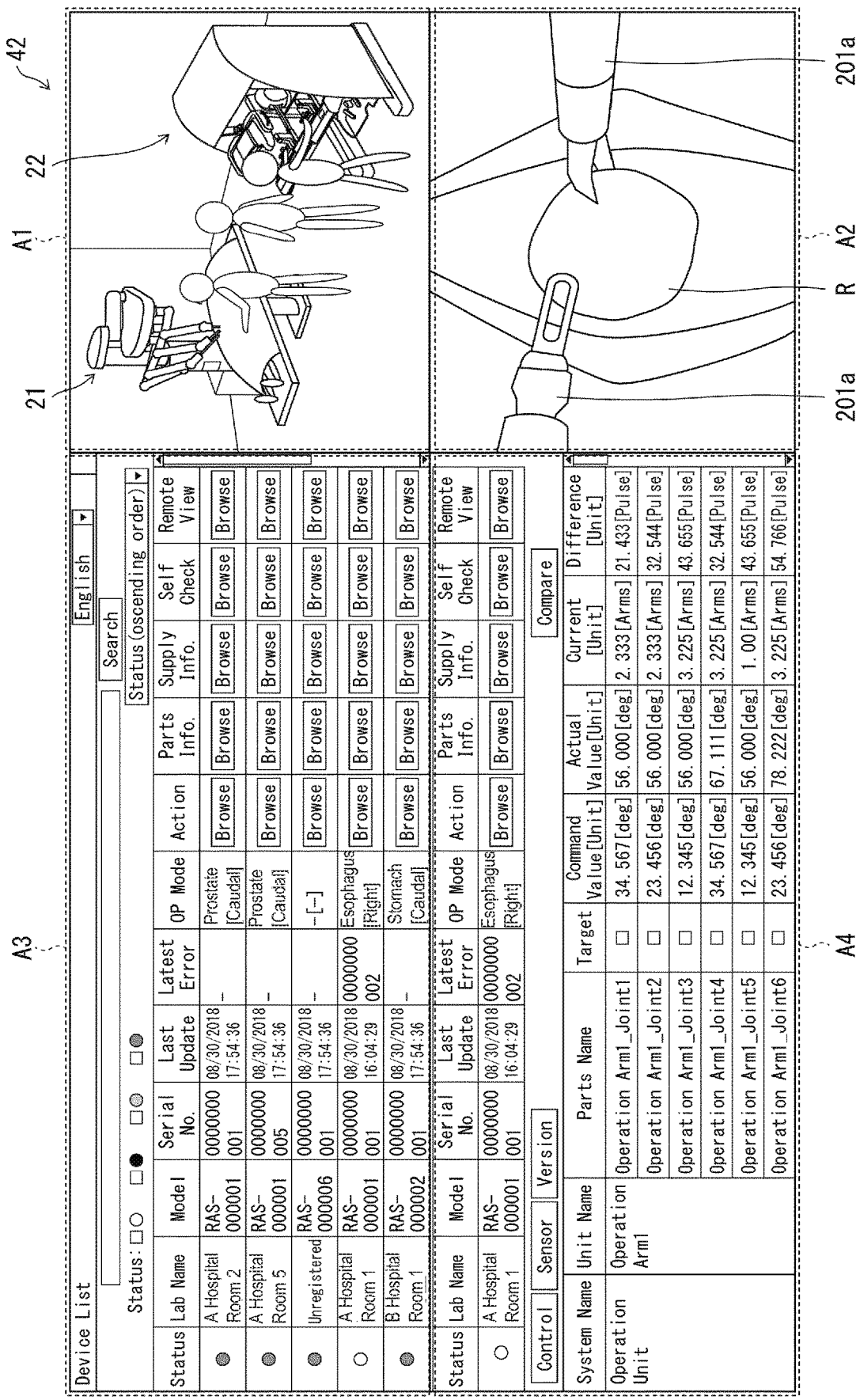
FIG. 15 is a schematic diagram illustrating an example of a display screen of a terminal device of a call center.
Figure 16:
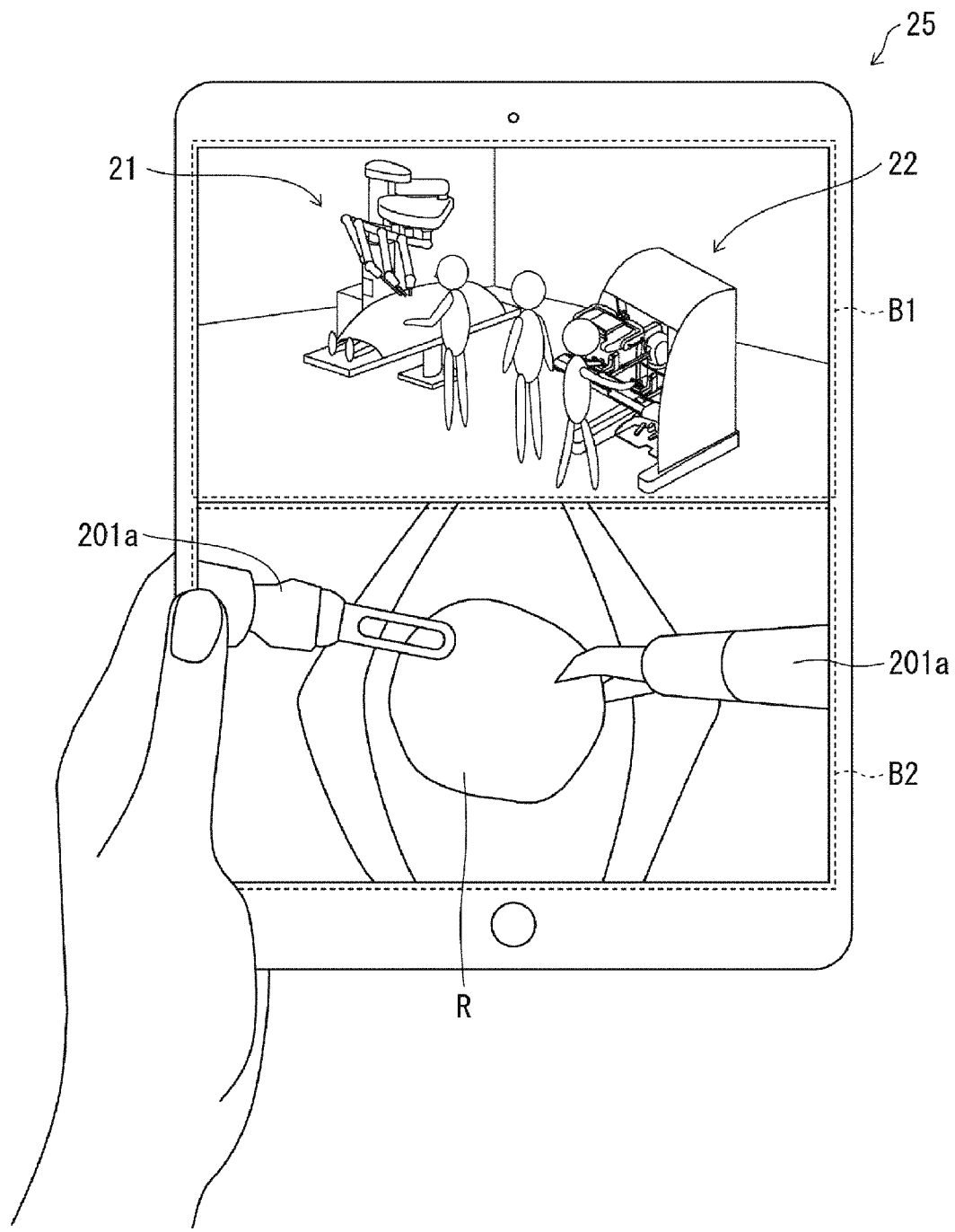
FIG. 16 is a schematic diagram illustrating an example of a display screen of a terminal device of a medical-related facility.

Examples of display screens of the monitors of the terminal device 42 and the terminal device 25 are explained with reference to FIGS. 15 to 17. FIG. 15 is a schematic diagram illustrating an example of the display screen of the monitor of the terminal device 42. FIG. 16 is a schematic diagram illustrating an example of the display screen of the monitor of the terminal device 25.

It is assumed that the bidirectional communication is established between the server device 40 and the terminal device 42 and the terminal device 25. It is assumed that an image of the operating room photographed by the network camera 24 and an image of the inside of the body cavity of the patient P photographed by the endoscope 201b are transmitted from the communication control unit 402 to the terminal device 42 and the terminal device 25.

The transmitted image of the operating room is displayed in a display region A1 (see FIG. 15) of the monitor of the terminal device 42 and a display region B1 (see FIG. 16) of the monitor of the terminal device 25. The patient-side device 21 and the remote operation device 22 are photographed in the image.

The transmitted image of the inside of the body cavity of the patient P is displayed in a display region A2 (see FIG. 15) of the monitor of the terminal device 42 and a display region B2 (see FIG. 16) of the monitor of the terminal device 25. Two instruments 201a introduced into the body of the patient P and a surgical site R are photographed in the image.

In this way, the same image is simultaneously displayed on both of the monitor of the terminal device 42 and the monitor of the terminal device 25. Consequently, both of the medical staff M and the serviceperson S can share a present state of the operating room and a present state of the inside of the body cavity of the patient P equivalently to or better than when the serviceperson S is present in the site. Therefore, the service person S can appropriately support the medical staff M.

In a region A3 illustrated in FIG. 15, operation information of the surgery assistant robots 20 acquired from the storage 41 is displayed for each surgery assistant robot 20. Specifically, a status (Status), a room name (Lab Name), a model (Model), a serial number (Serial No.), a last update date and time (Last update), a latest error (Latest Error), and an operation mode (OP Mode) are displayed and buttons (Browse) for displaying detailed screens concerning an action (Action), part information (Parts Info.), supply information (Supply Info.), self check (Self Check), and a remote view (Remote View) are displayed. In a display region A4 illustrated in FIG. 15, information concerning parts (Parts) of the surgery assistant robot 20 set in a first room of an A hospital is displayed in detail (Command Value, Actual Value, Current, and Difference). The serviceperson S can perform more accurate support by viewing these kinds of operation information.

Figure 17:
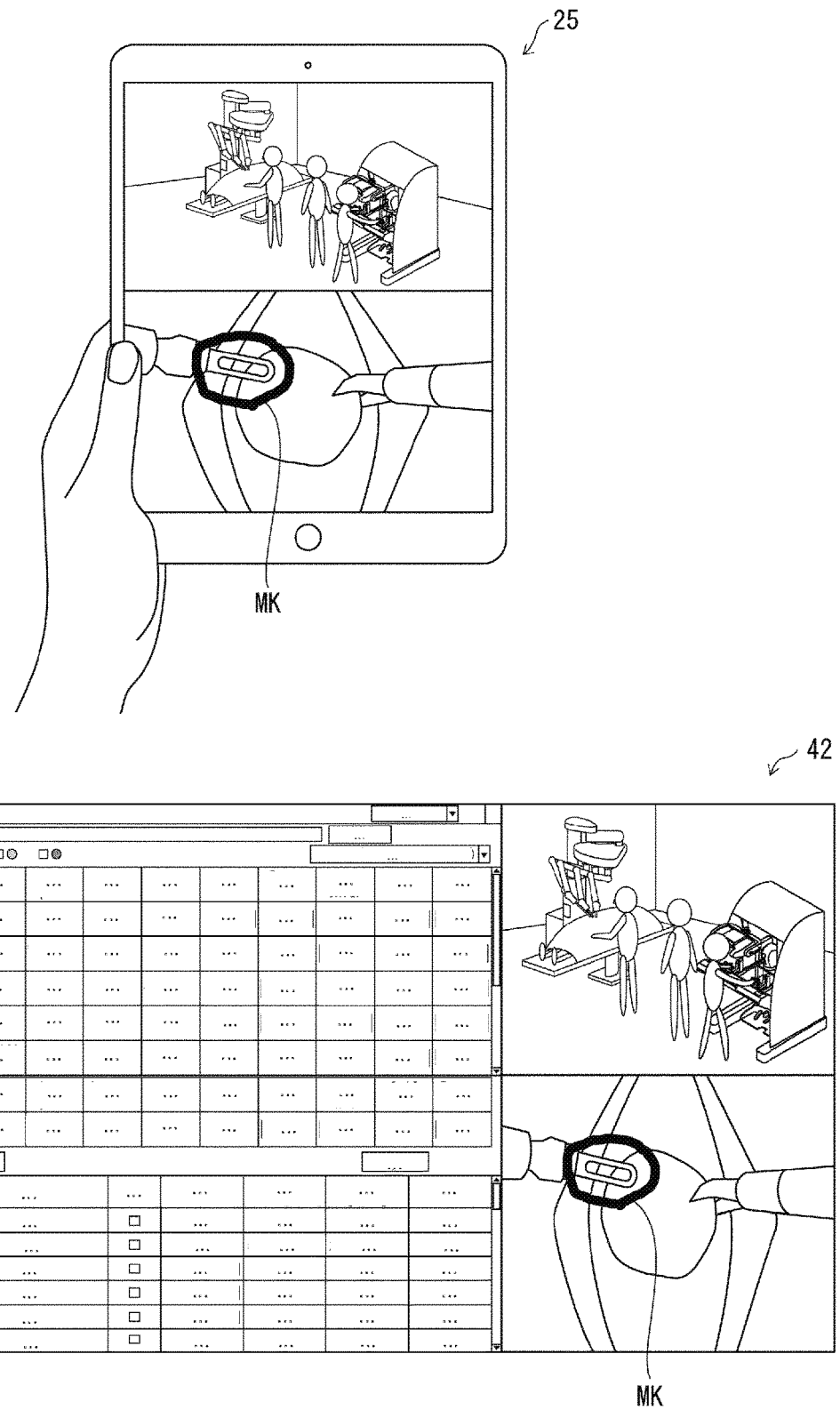
FIG. 17 is a schematic diagram illustrating an example of a state in which data is superimposed and displayed on display screens illustrated, such as in FIGS. 15 and 16.

FIG. 17 is a schematic diagram illustrating an example of a display screen on which data to be superimposed and displayed on an image is drawn by one of the terminal device 25 and the terminal device 42 in the states of the display screens illustrated in FIGS. 15 and 16. FIG. 17 illustrates a state in which marking MK drawn using a paint tool or the like by one of the terminal device 25 and the terminal device 42 is superimposed and displayed on images in both of the display screens. When the data superimposed on the image is drawn in this way by one of the terminal device 25 and the terminal device 42 with which the bidirectional communication is established, the processed image on which the data is superimposed and displayed is shared in both of the monitors of the terminal device 42 and the terminal device 25 according to the transmission by the communication control unit 402. Consequently, the medical staff M and the serviceperson S can easily share, for example, a noticeable part in the image.

[Modifications]

A sound input and output device and an image output device may be provided in the patient-side device 21 besides the touch panel 207. With the sound input and output device and the image output device, it is possible to perform operation for requesting establishment of the bidirectional communication in the patient-side device 21 and it is possible to perform, after the establishment of the bidirectional communication, bidirectional communication and data sharing between the medical staff M who uses the patient-side device 21 and the serviceperson S who uses the terminal device 42.

Similarly, an operation device that receives input operation, a sound input and output device, and an image output device may be provided in the remote operation device 22 besides the monitor 221. With the operation device, the sound input and output device, and the image output device, it is possible to perform operation for requesting establishment of the bidirectional communication in the remote operation device 22 and it is possible to perform, after the establishment of the bidirectional communication, bidirectional communication and data sharing between the medical staff M who uses the remote operation device 22 and the serviceperson S who uses the terminal device 42.

Similarly, an operation device that receives input operation, a sound input and output device, and an image output device may be connected to the image processing device 23 besides the monitor 231. With the operation device, the sound input and output device, and the image output device, it is possible to perform operation for requesting establishment of the bidirectional communication in the image processing device 23 and it is possible to perform, after the establishment of the bidirectional communication, bidirectional communication and data sharing between the medical staff M who uses the image processing device 23 and the serviceperson S who uses the terminal device 42.

The terminal device 25 is usually communicably connected to the intra-facility LAN. However, the terminal device 25 may be communicably connected to the external network 3 not via the intra-facility LAN.

Second Embodiment

Figure 18:
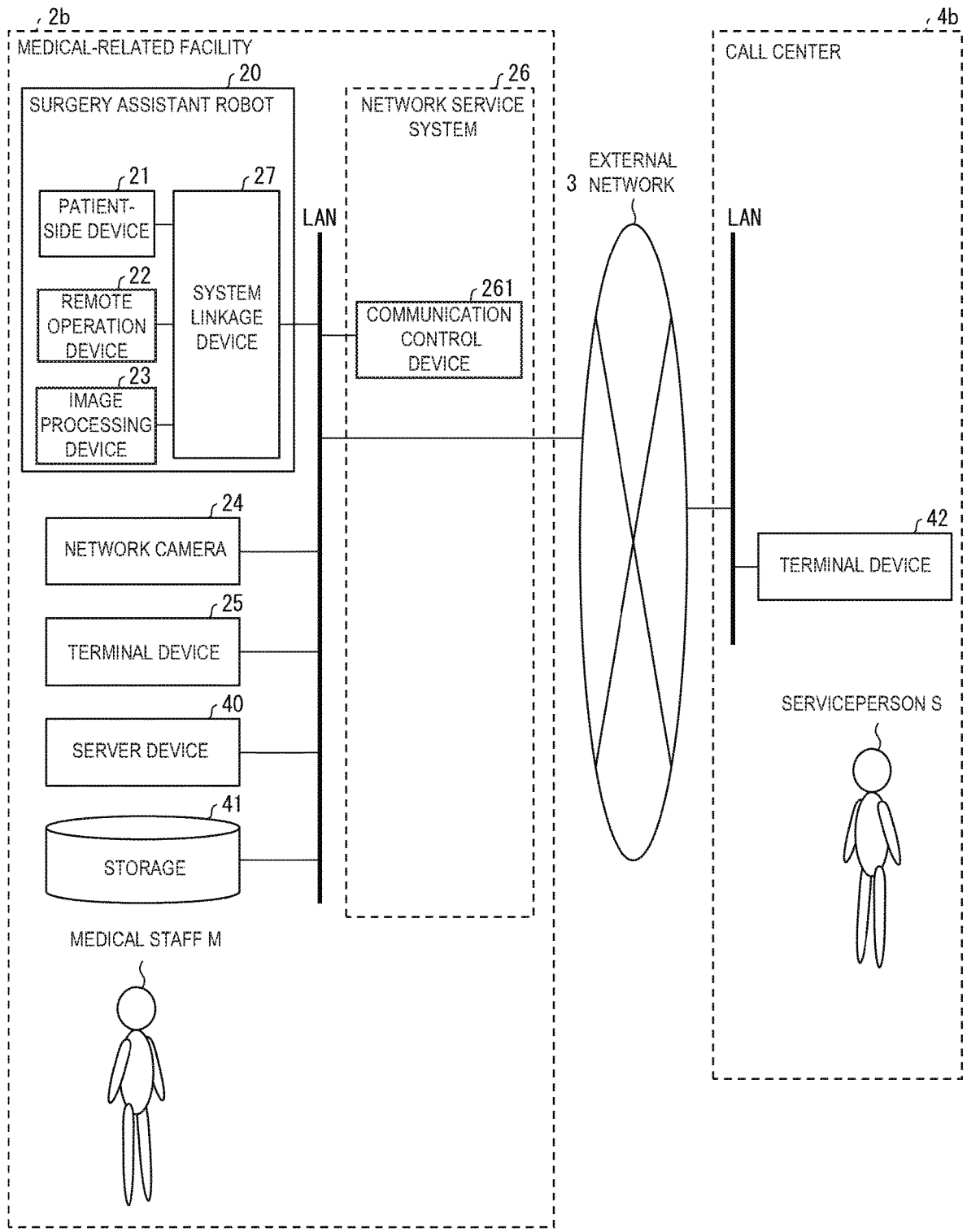
FIG. 18 is a diagram illustrating a schematic configuration of components that realize a remote support method according to a second embodiment.

The configuration example in which the server device 40 is installed in the call center 4 is explained above. However, a setting place of the server device 40 is not limited to this. As illustrated in FIG. 18, a medical-related facility 2b according to an embodiment is different from the medical-related facility 2 in a first embodiment in that the server device 40 and the storage 41 are set. The server device 40 and the storage 41 are communicably connected to a LAN provided in the medical-related facility 2b. A call center 4b according to an embodiment is different from the call center 4 in a first embodiment in that the server device 40 and the storage 41 are not set.

In an embodiment, transmission and reception of data between devices in the medical-related facility 2b and the server device 40 is performed via a LAN. Transmission and reception of data between the storage 41 and the terminal device 42 of the call center 4b and the server device 40 is performed via the external network 3.

Third Embodiment

The configuration example in which the surgery assistant robot 20 includes one patient-side device 21 including the surgical manipulators 201 is explained above. However, the configuration of the surgery assistant robot 20 is not limited to this. For example, the surgery assistant robot 20 may have a configuration including patient-side devices instead of the patient-side device 21 and each of the patient-side devices includes a manipulator to which a surgical instrument such as an endoscope or forceps is attached.

Figure 19:
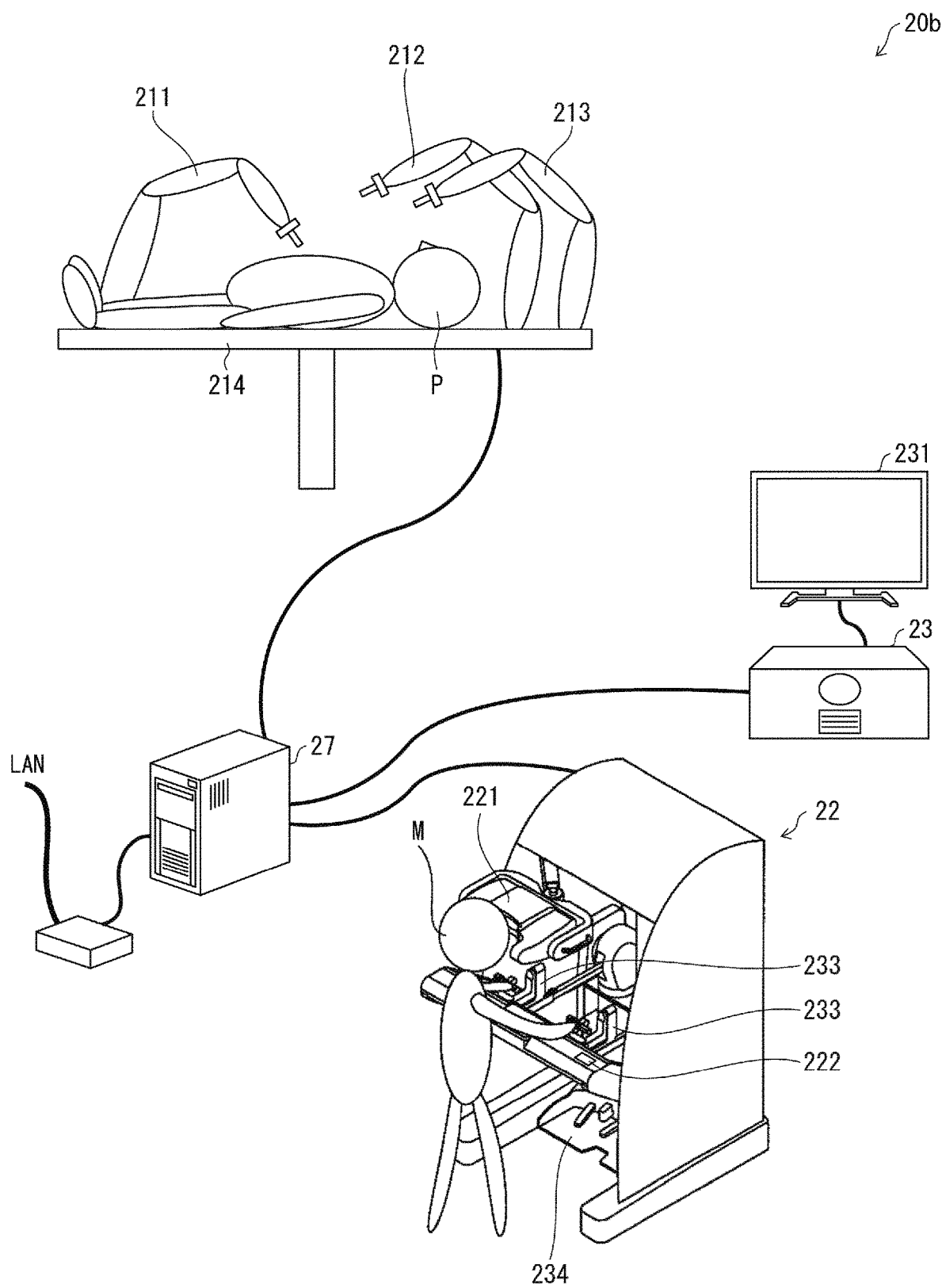
FIG. 19 is a diagram illustrating an overview of a surgery assistant robot according to a third embodiment.

A surgery assistant robot 20b according to an embodiment is illustrated in FIG. 19. The surgery assistant robot 20b is different from the surgery assistant robot 20 in that the surgery assistant robot 20b includes, instead of the patient-side device 21, three patient-side devices attached to a top plate 214 of an operating table on which the patient P is placed. Specifically, the surgery assistant robot 20b includes a first patient-side device 211 including a surgical manipulator (first manipulator) to which an endoscope is attached and a second patient-side device 212 and a third patient-side device 213 including surgical manipulators (second manipulators) to which surgical instruments such as forceps are attached. In the surgery assistant robot 20b, the remote operation device 22 transmits an operation command for operation that should be executed by the endoscope gripped by the surgical manipulator of the first patient-side device 211 to a controller of the first patient-side device 211 to thereby remotely operate the surgical manipulator of the first patient-side device 211. Similarly, the remote operation device 22 transmits an operation command for operation that should be executed by the surgical instrument gripped by the surgical manipulator of the second patient-side device 212 to a controller of the second patient-side device 212 to thereby remotely operate the surgical manipulator of the second patient-side device 212. Similarly, the remote operation device 22 transmits an operation command for operation that should be executed by the surgical instrument gripped by the surgical manipulator of the third patient-side device 213 to a controller of the third patient-side device 213 to thereby remotely operate the surgical manipulator of the third patient-side device 213.

In an embodiment, the communication control unit 402 performs processing of establishing the bidirectional communication between the server device 40 and at least one of the surgery assistant robot 20b (the first patient-side device 211, the second patient-side device 212, the third patient-side device 213, the remote operation device 22, and the image processing device 23) and the terminal device 25. In other words, the communication control unit 402 performs processing of establishing the bidirectional communication between the server device 40 and at least one of the surgery assistant robot 20b (the first patient-side device 211, the second patient-side device 212, the third patient-side device 213, the remote operation device 22, or the image processing device 23) or the terminal device 25.

Fourth Embodiment

The configuration example in which the surgery assistant robots 20 and 20b include the patient-side devices 21, 211, 212, and 213, the remote operation device 22, and the image processing device 23 is explained above. However, the configuration of the surgery assistant robot 20 is not limited to this.

A surgery assistant robot 20c according to an embodiment is illustrated in FIG. 20. The surgery assistant robot 20c includes a robot operating table 225 and an operation device 226. The robot operating table 225 includes a top plate 223 on which a patient is placed and a manipulator 224 for moving the top plate 223. One end of the manipulator 224 is fixed to a floor. The other end of the manipulator 224 supports the top plate 223. The operation device 226 is a mobile terminal for operating the robot operating table 225. The operation device 226 includes a button 227 for instructing a moving direction of the manipulator 224. The operation device 226 transmits an instruction input by the button 227 to a controller of the robot operating table 225. The manipulator 224 moves according to the instruction received by the controller and positions the top plate 223 in a desired position.

In the operation device 226, a button for communication 228 for requesting the bidirectional communication is provided. The medical staff M presses the button for communication 228, whereby a request for the bidirectional communication is transmitted from the operation device 226 to the server device 40. In an embodiment, the communication control unit 402 performs processing of establishing the bilateral communication between the server device 40 and at least one of the surgery assistant robot 20c (the robot operating table 225 and the operation device 226) and the terminal device 25. In other words, the communication control unit 402 performs processing of establishing the bilateral communication between the server device 40 and at least one of the surgery assistant robot 20c (the robot operating table 225 or the operation device 226) or the terminal device 25.

Note that the operation device 226 is capable of inputting and outputting data such as an image, a sound, and a text. After the establishment of the bidirectional communication, it is possible to perform bidirectional communication and the data sharing between the medical staff M who uses the operation device 226 and the serviceperson S who uses the terminal device 42. The image and the text are output to a monitor 229.

[Additional Note 1]

Timing when the medical staff M needs support by the serviceperson S could occur not only in a period in which the surgery assistant robot 20 is operating (that is, during surgery or training) but also in a period in which the surgery assistant robot 20 is not operating. For example, when the patient-side device 21, the remote operation device 22, and the image processing device 23 are connected by wire, in preparation before surgery and clean-up after the surgery, the medical staff M sometimes desires to seek support of the serviceperson S concerning wiring of these devices. Therefore, the bidirectional communication may be established in the period in which the surgery assistant robot 20 is not operating and bidirectional communication may be performed between the medical staff M and the serviceperson S.

[Additional Note 2]

As the bidirectional communication, there a form with which the bidirectional communication is performed between two devices and a form with which the bidirectional communication is performed among devices. A typical example of the former is suitable in a case in which the serviceperson S remotely supports one medical-related facility 2 (that is, a one-to-one relation). In this case, the bidirectional communication is performed between one terminal device 42 and the surgery assistant robot 20 or the terminal device 42. A typical example of the latter is suitable in a case in which an instructor remotely trains training target persons in training of the surgery assistant robot 20 (that is, a one-to-many relation). In this case, the bidirectional communication is performed between one terminal device 42 and the surgery assistant robots 20.

[Additional Note 3]

The server device 40 does not always need to be set in the facility of the call center 4 as in a first embodiment. The server device 40 may be set on the outside of the call center 4 and realized to be communicatively connected to the call center 4 via the external network 3.

[Additional Note 4]

In an embodiment, all the functions of the communication control device 261 do not always need to be included in the communication control device 261. For example, the surgery assistant robot 20 or the server device 40 may have a function of performing, on an image photographed by at least one of the endoscope 201b and the network camera 24, image processing of visually obscuring identifying information which enables a person to be identified and a function of adjusting a frame rate of an image photographed by at least one of the endoscope 201b and the network camera 24. In other words, the surgery assistant robot 20 or the server device 40 may have a function of performing, on an image photographed by at least one of the endoscope 201b or the network camera 24, image processing of visually obscuring identifying information which enables a person to be identified and a function of adjusting a frame rate of an image photographed by at least one of the endoscope 201b or the network camera 24.

[Additional Note 5]

In an embodiment, the request for the bidirectional communication is received by the server device 40, whereby the communication from the call center 4 to the medical-related facility 2 becomes possible. It goes without saying that, at emergency time, communication is possible from the call center 4 to the medical-related facility 2 even if the request for the bidirectional communication is not transmitted.

[Realization by Software]

Control blocks (in particular, the system linkage device 27) of the surgery assistant robots 20, 20b, and 20c, control blocks (in particular, the control unit 262) of the communication control device 261, and control blocks (in particular, the control unit 400) of the server device 40 may be realized by a logic circuit (hardware) formed on an integrated circuit (an IC chip) or may be realized by software.

In the latter case, the surgery assistant robots 20, 20b, and 20c, the communication control device 261, and the server device 40 include a computer that executes commands of programs, which are software, for realizing the functions. The computer includes, for example, one or more processors and includes a computer-readable recording medium storing the programs. In the computer, the processor reads the programs from the recording medium and executes the programs, whereby the object of one or more aspects is achieved. As the processor, for example, a CPU and a GPU (Graphics Processing Unit) can be used. As the recording medium, a "non-transitory tangible medium", a tape, a disk, a card, a semiconductor memory, a programmable logic circuit, and the like can be used besides, for example, a ROM (Read Only Memory). The computer may further include a RAM (Random Access Memory) on which the programs are developed. The programs may be supplied to the computer via any transmission medium (a communication network, a broadcasting wave, or the like) capable of transmitting the programs. Note that an embodiment can also be realized in a form of a data signal embedded in a carrier wave in which the programs are embodied by electronic transmission.

The present invention is not limited to the embodiments explained above. Various changes are possible in a range described in claims. An embodiment obtained by combining, as appropriate, the technical means respectively disclosed in the different embodiments is also included in the technical scope of the present invention.

The invention claimed is:

1. A method of remotely supporting a surgery assistant robot, comprising:
  receiving at least one piece of operation information concerning an operation of the surgery assistant robot, by a server device via an external network that performs a remote support for the surgery assistant robot during the operation thereof, wherein the server device is located in a facility different from a medical facility where the surgery assistant robot is located;
  storing the operation information in a storage data-communicably connected to the server device;
  detecting an abnormality in the surgery assistant robot, or an abnormal situation in the vicinity of the surgery assistant robot, based on the at least one piece of operation information;
  establishing, in response to a request for bidirectional communication transmitted from the surgery assistant robot or a terminal device in the medical facility where the surgery assistant robot is located, based on detecting the abnormality; or in response to detecting the abnormality or the abnormal situation by the server device, a bidirectional communication between the server device and at least one of the surgery assistant robot or the terminal device to perform the remote support for the surgery assistant robot during the operation thereof;

transmitting data generated by processing the operation information, using the established bidirectional communication, from the server device to at least one of the surgery assistant robot or the terminal device via the external network to perform the remote support; and storing, in the storage, during the period in which the bidirectional communication is established, the transmitted data as a log of the bidirectional communication.

2. The method according to claim 1, wherein the operation information comprises an image photographed by the surgery assistant robot.

3. The method according to claim 2, further comprising: receiving, by the server device, data to be superimposed on the image.

4. The method according to claim 3, further comprising: transmitting, after the bidirectional communication is established, a processed image, on which the data is superimposed on the image, from the server device to at least one of the surgery assistant robot or the terminal device.

5. The method according to claim 1, further comprising: receiving, by the server device, the at least one piece of operation information comprising an image photographed by a camera that photographs an inside of a room in which the surgery assistant robot is installed.

6. The method of remotely supporting a surgery assistant robot according to claim 1, further comprising:
adjusting a frame rate of an image photographed by at least one of the surgery assistant robot or a camera that photographs an inside of a room in which the surgery assistant robot is installed; and
transmitting the image, the frame rate of which is adjusted, to the server device, wherein:
the image is transmitted via the external network.

7. The method of remotely supporting a surgery assistant robot according to claim 1, further comprising:
processing an image photographed by at least one of the surgery assistant robot or a camera that photographs an inside of a room where the surgery assistant robot is installed, by image processing of visually obscuring identifiable information that enables a person to be identified; and
transmitting an image obtained by the image processing to the server device, wherein
the image is transmitted via the external network.

8. The method according to claim 1, further comprising: analyzing the operation information by the server device as the processing, wherein
the data transmitted from the server device to at least one of the surgery assistant robot or the terminal device comprises data generated by the analyzing.

9. The method according to claim 1, further comprising: selecting one of application programs installed the server device; and
analyzing the operation information by the server device, using the application program, as the processing, wherein the data transmitted from the server device to at least one of the surgery assistant robot or the terminal device comprises data generated by the analyzing.

10. The method of remotely supporting a surgery assistant robot according to claim 1, wherein detecting the abnormality in the surgery assistant robot, comprises:
detecting the abnormality by the surgery assistant robot; and
transmitting the request for bidirectional communication from the surgery assistant robot in response to an operation of a switch or a button on the surgery assistant robot after the abnormality is detected.

11. The method of remotely supporting a surgery assistant robot according to claim 1, wherein detecting the abnormality in the surgery assistant robot, comprises:
detecting the abnormality by the surgery assistant robot; and
transmitting the request for bidirectional communication from the terminal device in response to an operation of a button on the terminal device after the abnormality is detected.

12. A remote support system comprising:
a server device; and
a storage data-communicably connected to the server device, wherein
the server device receives operation information via an external network concerning an operation of a surgery assistant robot during the operation thereof and stores the operation information in the storage,
in response to a request for bidirectional communication received from at least one of the surgery assistant robot or a terminal device in a medical facility in which the surgery assistant robot is installed; or in response to detecting an abnormality in the surgery assistant robot or an abnormal situation in the vicinity of the surgery assistant robot from the operation information, the server device establishes bidirectional communication between at least one of the surgery assistant robot or the terminal device to perform a remote support for the surgery assistant robot during the operation thereof,
the server device transmits data generated by processing the operation information, using the bidirectional communication, to at least one of the surgery assistant robot or the terminal device via the external network to perform the remote support,
the storage stores, during the period in which the bidirectional communication is established, the transmitted data as a log of the bidirectional communication, and
the server device is located in a facility different from the medical facility.

13. The remote support system according to claim 12, wherein
the server device is communicatively connected to the surgery assistant robot and at least one surgery assistant robot other than the surgery assistant robot.

14. The remote support system according to claim 12, wherein
the surgery assistant robot comprises:
a patient-side device comprising a first manipulator to which an endoscope is attached and a second manipulator to which a surgical instrument is attached; and
a remote operation device that remotely operates the first manipulator and the second manipulator.

15. The remote support system according to claim 14, wherein the surgery assistant robot further comprises an image processing device that applies image processing to an image photographed by the endoscope.

16. The remote support system according to claim 12, wherein
the surgery assistant robot comprises:
a first patient-side device comprising a first manipulator to which an endoscope is attached;
a second patient-side device comprising a second manipulator to which a surgical instrument is attached; and
a remote operation device that remotely operates the first manipulator and the second manipulator.

17. The remote support system according to claim 12, wherein
the surgery assistant robot comprises:
a robot operating table comprising a top plate on which a patient is placed and a manipulator that moves the top plate; and
an operation device that operates the robot operating table.

18. The remote support system according to claim 12, wherein
the server device receives an image photographed by a photographing device that photographs a state of a room in which the surgery assistant robot is installed.

19. The remote support system according to claim 18, further comprising a communication control device installed in the medical facility, wherein
the communication control device determines whether the image includes identifiable information that enables a person to be identified, and
in a case in which the identifiable information is determined to be included, the communication control device performs image processing of visually obscuring the identifiable information and transmits, to the server device, an image obtained by the image processing.

20. The remote support system according to claim 19, wherein
the communication control device transmits the image photographed by the photographing device to the server device via a communication network, and
the communication control device monitors a communication load of the communication network and adjusts a frame rate of the image according to the communication load.

21. The remote support system according to claim 12, further comprising a second terminal device connected to the server device, wherein
the server device receives an image photographed by an endoscope attached to the surgery assistant robot and transmits the received image to at least the second terminal device after the bidirectional communication is established.

22. The remote support system according to claim 21, wherein the server device transmits both of an image photographed by a camera that photographs a state of a room in which the surgery assistant robot is installed and an image photographed by an endoscope attached to the surgery assistant robot to at least the second terminal device after the bidirectional communication is established.

23. The remote support system according to claim 21, wherein,
in response to an input of data to be superimposed on the image at the second terminal device, the server device transmits the data to at least one of the surgery assistant robot or the terminal device.

* * * * *